US010219494B2

(12) United States Patent
McWhirter et al.

(10) Patent No.: US 10,219,494 B2
(45) Date of Patent: *Mar. 5, 2019

(54) NON-HUMAN ANIMALS HAVING A HUMANIZED B-CELL ACTIVATING FACTOR GENE

(71) Applicant: Regeneron Pharmaceuticals, Inc., Tarrytown, NY (US)

(72) Inventors: John McWhirter, Hastings-on-Hudson, NY (US); Cagan Gurer, Chappaqua, NY (US); Lynn Macdonald, Harrison, NY (US); Andrew J. Murphy, Croton-on-Hudson, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/459,453

(22) Filed: Mar. 15, 2017

(65) Prior Publication Data

US 2017/0188556 A1    Jul. 6, 2017

Related U.S. Application Data

(63) Continuation of application No. 14/561,926, filed on Dec. 5, 2014, now Pat. No. 9,629,347, which is a continuation of application No. 14/537,312, filed on Nov. 10, 2014.

(60) Provisional application No. 61/905,983, filed on Nov. 19, 2013.

(51) Int. Cl.
*A01K 67/027*    (2006.01)
*C07K 14/705*    (2006.01)
*G01N 33/50*    (2006.01)

(52) U.S. Cl.
CPC .... *A01K 67/0278* (2013.01); *C07K 14/70575* (2013.01); *G01N 33/5088* (2013.01); *A01K 2207/12* (2013.01); *A01K 2207/15* (2013.01); *A01K 2217/07* (2013.01); *A01K 2217/072* (2013.01); *A01K 2227/105* (2013.01); *A01K 2267/03* (2013.01); *A01K 2267/0325* (2013.01); *A01K 2267/0381* (2013.01); *A01K 2267/0387* (2013.01); *C07K 2319/00* (2013.01); *G01N 2500/10* (2013.01)

(58) Field of Classification Search
CPC ................ A01K 67/0278; C07K 14/70575
See application file for complete search history.

(56) References Cited

U.S. PATENT DOCUMENTS 7,759,541 B2 *  7/2010  Wolf .................. A01K 67/0276
                                                                800/18
2015/0143558 A1   5/2015  McWhirter et al.
2015/0143561 A1   5/2015  McWhirter et al.

FOREIGN PATENT DOCUMENTS

| EA | 006108 B1 | 2/2002 |
|---|---|---|
| WO | 2004/016737 A2 | 2/2004 |
| WO | 2006/031718 A2 | 3/2006 |
| WO | WO/2006/128163 * | 5/2006 |
| WO | 2006/128163 A2 | 11/2006 |
| WO | 2011/031835 A1 | 3/2011 |
| WO | 2012/112544 A2 | 8/2012 |
| WO | WO/2012/112544 * | 8/2012 |
| WO | 2013/063556 A1 | 5/2013 |
| WO | 2013/158577 A1 | 10/2013 |

OTHER PUBLICATIONS

Gavin J Immunol. 175, 319-328), (Year: 2005).*
Schmidt et al PLoS One, vol. 3, No. 9, e3192 (Year: 2008).*
Willinger et al Trends in Immunology, vol. 32, No. 7, 321-327 (Year: 2011).*
Bossen et al Seminars in Immunology 18 , 263-275 (Year: 2006).*
Willinger et al Trends in Immunology, 32, 7, 321-327 (Year: 2011).*
Anderson P., "Post-Transcriptional Control of Cytokine Production", Nature Immunology 9(4):353-359 (Apr. 2008).
Batten M. et al., "TNF Deficiency Fails to Protect BAFF Transgenic Mice against Autoimmunity and Reveals a Predisposition to B Cell Lymphoma", The Journal of Immunology 172(2):812-822 (Jan. 2004).
Bossen C. et al., "BAFF, APRIL and Their Receptors: Structure, Function and Signaling", Seminars in Immunology 18:263-275 (2006).
Carpenter S. et al., "Post-Transcriptional Regulation of Gene Expression in Innate Immunity", Nature Reviews, Immunology 14:361-376 (Jun. 2014).
Clark J. et al., "A Future for Transgenic Livestock", Nature Reviews—Genetics 4:825-833 (Oct. 2003).
Gavin A.L. et al., "DeltaBAFF, a Splice Isoform of BAFF, Opposes Full-Length BAFF Activity In Vivo in Transgenic Mouse Models", The Journal of Immunology 175(1):319-328 (Jul. 2005).
Gavin A.L. et al., "BAFF, a Splice Isoform of BAFF, Opposes Full-Length BAFF Activity In Vivo in Transgenic Mouse Models", The Journal of Immunology 175:319-328 (2005).
Gibbs R.A. et al., "Genome Sequence of the Brown Norway Rat Yields Insights into Mammalian Evolution", Nature 428:492-521 (Apr. 1, 2004).
Greiner D.L. et al., "Humanized Mice for the Study of Type 1 and Type 2 Diabetes", Annals of the New York Academy of Sciences 1245(1):55-58 (Dec. 29, 2011).

(Continued)

*Primary Examiner* — Anoop K Singh
(74) *Attorney, Agent, or Firm* — Scully, Scott, Murphy & Presser, P.C.; Elysa Goldberg

(57) ABSTRACT

Non-human animals, cells, methods and compositions for making and using the same are provided, wherein the non-human animals and cells comprise a humanized B-cell activating factor gene. Non-human animals and cells that express a human or humanized B-cell activating factor protein from an endogenous B-cell activating factor locus are described.

10 Claims, 2 Drawing Sheets

Specification includes a Sequence Listing.

(56) References Cited

OTHER PUBLICATIONS

Hong J. et al., "Derivation and Characterization of Embryonic Stem Cells Lines Derived from Transgenic Fischer 344 and Dark Agouti Rates", Stem Cells and Development 21(9):1571-1586 (2012).
Huang, W. et al., "BAFF/APRIL Inhibition Decreases Selection of Naive But Not Antigen-Induced Autoreactive B Cells in Murine Systemic Lupus Erythematosus", The Journal of Immunology 187(12):6571-6580 (Dec. 2011).
Jacob H.J. et al., "Gene Targeting in the Rat: Advances and Opportunities", Trends in Genetics 26(12):510-518 (Dec. 2010).
Keefer C.L., "Lessons Learned from Nuclear Transfer (Cloning)", Theriogenology 69:48-54 (2008).
Khare S.D. et al., "Severe B Cell Hyperplasia and Autoimmune Disease in TALL-1 Transgenic Mice", PNAS 97(7):3370-3375 (Mar. 2000).
Kreuzaler M. et al., "Soluble BAFF Levels Inversely Correlate With Peripheral B Cell Numbers and the Expression of BAFF Receptors", The Journal of Immunology 188(1):497-503 (Jan. 1, 2012).
Krzywinski M. et al., "Integrated and Sequence-Ordered BAC-and YAC-Based Physical Maps for the Rat Genome", Genome Research 14:766-779 (2004).
Mackay F. et al., "BAFF: A Fundamental Survival Factor for B Cells", Nature Reviews—Immunology 2(7):465-475 (Jul. 2002).
Mackay, F. et al., "Mice Transgenic for BAFF Develop Lymphocytic Disorders Along with Autoimmune Manifestations", J. Exp. Med. 190(11):1697-1710 (Dec. 1999).
McCarthy D.D. et al., "Mice overexpressing BAFF Develop a Commensal Flora—Dependent, IgA—Associated Nephropathy", The Journal of Clinical Investigation 121(10):3991-4002 (Oct. 2011).
Munoz M. et al., "Constraints to Progress in Embryonic Stem Cells from Domestic Species", Stem Cell Rev and Rep 5:6-9 (2009).
Niemann H. et al. "Transgenic Farm Animals: Present and Future", Rev. Sci. Tech. Off. Int. Epiz. 24(1):285-298 (2005).
Osoegawa K. et al., "BAC Resources for the Rat Genome Project", Genome Research 780-785 (2004).
Ota M. et al., "Regulation of the B Cell Receptor Repertoire and Self-Reactivity by BAFF", The Journal of Immunology 185(7):4128-4136 (Oct. 2010).
Rickert R.C. et al., "Signaling by the TNFR Superfamily in B-Cell Biology and Disease", Immunol Rev. 244(1):115-133 (Nov. 2011).
Ristevski S., "Making Better Transgenic Models—Conditional, Temporal, and Spatial Approaches", Molecular Biotechnology 29:153-163 (2005).
Rongvaux A. et al., "Human Thrombopoietin Knockin Mice Efficiently Support Human Hematopoiesis In Vivo", Proc. Natl. Acad. Sci. USA 108(5):2378-2383 (Feb. 2011).
Schmidt M.R. et al., "Human BLyS Facilitates Engraftment of Human PBL Derived B Cells in Immunodeficient Mice", PLOS One 3(9):e3192, pp. 1-10 (Sep. 11, 2008).
Shultz L.D. et al., "Humanized Mice for Immune System Investigation: Progress, Promise and Challenges", Nature Reviews Immunology 12(11):786-798 (Nov. 2012).
Sigmund C.D., "Viewpoint: Are Studies in Genetically Altered Mice Out of Control?", Arterioscler Thromb Vasc Biol. 20:1425-1429 (Jun. 2000).
Smith K.R., "Gene Transfer in Higher Animals: Theoretical Considerations and Key Concepts", Journal of Biotechnology 99:1-22 (2002).
Sosa M A G et al., "Animal Transgenesis: An Overview", Brain Struct Funct 214:91-109 (2010).
Stice S.L. et al., "Cloning: New Break Throughs Leading to Commercial Opportunities", Theriogenology 49:129-138 (1998).
Tong C. et al., "Production of p53 Gene Knockout Rats by Homologous Recombination in Embryonic Stem Cells", Nature 467:211-215 (Sep. 9, 2010).
Van Der Weyden L. et al., "Tools for Targeted Manipulation of the Mouse Genome", Physiol Genomics 11:133-164 (2002).
Walters S. et al., "Increased CD4+Foxp3+ T Cells in BAFF-Transgenic Mice Suppress T Cell Effector Responses", The Journal of Immunology 182(2):793-801 (Jan. 2009).
Wheeler M.B. et al., "Transgenic Technology and Applications in Swine", Theriogenology 56:1345-1369 (2001).
Willinger T. et al., "Human IL-3/GM-CSF Knock-In Mice Support Human Alveolar Macrophage Development and Human Immune Responses in the Lung", Proc. Natl. Acad. Sci. USA 108(5):2390-2395 (Feb. 2011).
Willinger T. et al., "Improving Human Hemato-Lymphoid-System Mice by Cytokine Knock-In Gene Replacement", Trends in Immunology 32(7):321-327 (Jul. 2011).
Yanagimachi R., "Cloning: Experience from the Mouse and Other Animals", Molecular and Cellular Endocrinology 187:241-248 (2002).
GenBank Accession No. NM_006573.4 (5 pages) (Jan. 14, 2016).
GenBank Accession No. NM_033622.1 (4 pages) (Feb. 15, 2015).
GenBank Accession No. NW_003812287.1 (11 pages) (Dec. 9, 2013).
GenBank Accession No. XM_006253480.1 (2 pages) (Dec. 9, 2013).
Ensembl Transcript Tnfsf13b-201 (1 page) (Sep. 2013).
International Search Report and Written Opinion dated Mar. 5, 2015 issued in International Application No. PCT/US2014/064806.
Dennis Jr. M.B., "Welfare Issues of Genetically Modified Animals", ILAR Journal 43(2):100-109 (2002).
Zhou H. et al., "Developing tTA Transgenic Rats for Inducible and Reversible Gene Expression", International Journal of Biological Sciences 5:171-181 (2009).
Russian Office Action and Search Report dated Apr. 3, 2018 received in Russian Patent Application No. 2016123708, together with an English-language translation.
Extended European Search Report dated Oct. 17, 2018 received in European Patent Application No. 18 18 5303.7.

* cited by examiner

NON-HUMAN ANIMALS HAVING A HUMANIZED B-CELL ACTIVATING FACTOR GENE

CROSS REFERENCE TO RELATED APPLICATION

This application is a continuation of U.S. patent application Ser. No. 14/561,926, filed Dec. 5, 2014, which is a continuation of U.S. patent application Ser. No. 14/537,312, filed Nov. 10, 2014, which claims the benefit of priority of U.S. Provisional Application No. 61/905,983, filed Nov. 19, 2013, the entire contents of which are incorporated herein by reference.

BACKGROUND

Autoimmunity results when an organism's natural mechanisms for preventing its immune system from attacking its own cells and tissues break down. Diseases, disorders and conditions caused by breakdown, and by the aberrant self-directed immune responses that result, are referred to as autoimmune diseases. Notable examples of autoimmune diseases, disorders and conditions include diabetes mellitus, systemic lupus erythematosus (SLE), rheumatoid arthritis (RA) and some allergies. Autoimmune diseases are estimated to be among the ten leading causes of death. Investment in the development of therapies for autoimmune diseases is in the multi-billion dollar range and critical in vivo systems to test, develop and validate candidate therapeutics are necessary to ensure treatment safety and effectiveness. Further, such in vivo systems are necessary in determining if new treatments can sustain long term improvement in patients and, perhaps, can even provide cures for many diseases that remain unaddressed. Such in vivo systems also provide a source for assays in human hematopoietic and immune system related functions in vivo, identification of novel therapies and vaccines.

SUMMARY OF INVENTION

The present invention encompasses the recognition that it is desirable to engineer non-human animals to provide improved in vivo autoimmune disease systems to permit the testing, development and validation of new and existing candidate therapeutics. The present invention also encompasses the recognition that it is desirable to engineer non-human animals to permit improved activation and survival of human lymphocytes (e.g., B cells) post-immunization and post-engraftment of human hematopoietic stem cells or B cells from human donors. The present invention also encompasses the recognition that non-human animals having a humanized Baff gene and/or otherwise expressing, containing, or producing a human or humanized Baff protein are desirable, for example for use in engraftment of human hematopoietic stem cells or B cells from human donors.

In some embodiments, a non-human animal of the present invention expresses a Baff polypeptide comprising the extracellular portion of a human BAFF protein linked to the intracellular portion of a mouse Baff protein.

In some embodiments, an extracellular portion of a human BAFF protein is encoded by exons 3 to 6 of a human BAFF gene.

In some embodiments, exons 3 to 6 of a human BAFF gene are at least 50%, at least 55%, at least 60%, at least 65%, at least 70%, at least 75%, at least 80%, at least 85%, at least 90%, at least 95%, or at least 98% identical with exons 3 to 6 of a human BAFF gene that appears in Table 3. In some embodiments, exons 3 to 6 of a human BAFF gene are 100% identical with exons 3 to 6 of a human BAFF gene that appears in Table 3.

In some embodiments, a non-human animal of the present invention does not detectably express a full-length endogenous Baff protein. In some embodiments, the non-human animal is a rodent and does not detectably express a full-length rodent Baff protein. In some embodiments, the non-human animal is a mouse and does not detectably express a full-length mouse Baff protein whose sequence appears in Table 3.

In some embodiments, a Baff polypeptide of the present invention is expressed from a genetically modified Baff gene at an endogenous non-human Baff locus. In some certain embodiments, a genetically modified Baff gene comprises a non-human Baff exon 1. In some certain embodiments, a genetically modified Baff gene comprises a non-human Baff exon 2. In some certain embodiments, a genetically modified Baff gene comprises a non-human Baff exon 7 in whole or in part. In some certain embodiments, a genetically modified Baff gene comprises a non-human Baff exon 1 and exon 2. In some certain embodiments, a genetically modified Baff gene comprises a non-human Baff exon 1, a non-human Baff exon 2, a non-human Baff exon 7 in whole or in part, or a combination thereof. In various embodiments, a non-human Baff exon 7 in part comprises a non-human Baff 3' untranslated region (UTR) and a non-human Baff polyadenylation signal.

In some embodiments, the present invention provides a non-human animal comprising a genetically modified Baff gene that comprises one or more exons of a human BAFF gene (i.e., a humanized Baff gene) operably linked to a Baff promoter. In some embodiments, a Baff promoter of the present invention is a non-human Baff promoter. In some embodiments, a BAFF promoter of the present invention is a human Baff promoter.

In some embodiments, a humanized Baff gene of the present invention comprises exons 3 to 6 of a human BAFF gene. In some certain embodiments, a humanized Baff gene further comprises a non-human Baff exon 1. In some certain embodiments, a humanized Baff gene further comprises a non-human Baff exon 2. In some certain embodiments, a humanized BAFF gene further comprises a non-human Baff exon 7 in whole or in part. In some certain embodiments, a humanized Baff gene comprises a non-human Baff exon 1, exon 2 and a non-human Baff exon 7 in whole or in part. In various embodiments, a non-human Baff exon 7 in part comprises a non-human Baff 3' untranslated region (UTR) and a non-human Baff polyadenylation signal.

In some embodiments, exons 3 to 6 of a human BAFF gene are at least 50%, at least 55%, at least 60%, at least 65%, at least 70%, at least 75%, at least 80%, at least 85%, at least 90%, at least 95%, or at least 98% identical with exons 3 to 6 of a human BAFF gene that appears in Table 3. In some embodiments, exons 3 to 6 of a human BAFF gene are 100% identical with exons 3 to 6 of a human BAFF gene that appears in Table 3.

In various embodiments, a non-human animal of the present invention is a rodent. In some certain embodiments, a rodent of the present invention is selected from a mouse or a rat.

In some embodiments, the present invention provides a humanized Baff locus (or gene) comprising one or more exons of a non-human Baff gene operably linked to one or more exons of a human BAFF gene.

In some embodiments, a humanized Baff locus (or gene) of the present invention comprises non-human Baff exons 1 and 2 operably linked to human BAFF exons 3 to 6. In some certain embodiments, a humanized Baff locus (or gene) further comprises 5' and 3' non-human untranslated regions (UTRs) flanking a non-human Bat exon 1 and a human BAFF exon 6.

In some embodiments, the present invention provides a Baff polypeptide encoded by a humanized Baff locus, or gene, as described herein.

In some embodiments, the present invention provides a cell or tissue isolated from a non-human animal as described herein. In some embodiments, a cell is selected from an astrocyte, dendritic cell, lymphocyte (e.g., a B or T cell), monocyte, neutrophils and a stromal cell. In some embodiments, a tissue is selected from adipose, bladder, brain, breast, bone marrow, eye, heart, intestine, kidney, liver, lung, lymph node, muscle, pancreas, plasma, serum, skin, spleen, stomach, thymus, testis, ovum, and/or a combination thereof.

In some embodiments, the present invention provides an isolated non-human (e.g., rodent) cell or tissue whose genome includes a Baff gene (or locus) comprising one or more exons of a non-human Baff gene operably linked to one or more exons of a human BAFF gene. In some certain embodiments, the present invention provides an isolated non-human (e.g., rodent) cell or tissue whose genome includes a Bali gene (or locus) comprising non-human Baff exons 1 and 2 operably linked to human BAFF exons 3 to 6, wherein the Baff gene (or locus) further comprises 5' and 3' non-human untranslated regions (UTRs) flanking the non-human Baff exon 1 and the human BAFF exon 6. In some embodiments, a Baff gene (or locus) comprises a sequence that encodes a BAFF polypeptide that comprises residues 142 to 285 of a human BAFF protein.

In some embodiments, the present invention provides a non-human embryonic stem (ES) cell whose genome comprises a Baff gene (or locus) as described herein. In some certain embodiments, the ES cell comprises a Baff gene that encodes the extracellular portion of a human BAFF protein linked to the intracellular portion of a mouse Baff protein. In some certain embodiments, the ES cell comprises a Baff gene that comprises exons 3 to 6 of a human BAFF gene. In some certain embodiments, the ES cell is a rodent ES cell. In some embodiments, a non-human ES cell of the present invention is a mouse or rat ES cell.

In some embodiments, the present invention provides the use of a non-human embryonic stem cell as described herein to make a non-human animal. In some certain embodiments, a non-human embryonic stem cell is murine and is used to make a mouse comprising a Baff gene as described herein.

In some embodiments, the present invention provides a non-human embryo comprising, made from, obtained from, or generated from a non-human embryonic stem cell comprises a Baff gene as described herein. In some embodiments, a non-human embryo of the present invention is a rodent embryo. In some embodiments, a rodent embryo as described herein is a mouse or rat embryo.

In some embodiments, the present invention provides a method of making a non-human animal that expresses a Baff protein from a humanized Baff gene at an endogenous Baff locus, wherein the Baff protein comprises a human sequence, the method comprising the steps of targeting an endogenous Baff gene (or locus) in a non-human embryonic stem (ES) cell with a genomic fragment comprising a human nucleotide sequence that encodes a human BAFF protein in whole or in part, obtaining a modified non-human embryonic stem (ES) cell comprising a humanized Baff gene at an endogenous Baff locus that comprises said human sequence, and creating a non-human animal using said modified embryonic stem (ES) cell.

In some embodiments, said human nucleotide sequence comprises exons 3 to 6 of a human BAFF gene. In some embodiments, said human nucleotide sequence comprises exons 3 to 6 of a human BAFF gene that are at least 50%, at least 55%, at least 60%, at least 65%, at least 70%, at least 75%, at least 80%, at least 85%, at least 90%, at least 95%, or at least 98% identical with exons 3 to 6 of a human BAFF gene that appears in Table 3. In some certain embodiments, said human nucleotide sequence comprises exons 3 to 6 of a human BAFF gene that are 100% identical with exons 3 to 6 of a human BAFF gene that appears in Table 3.

In some embodiments, said human nucleotide sequence encodes amino acid residues 142 to 285 of a human BAFF protein. In some embodiments, said human nucleotide sequence encodes amino acid residues 142-285 of a human BAFF protein that are at least 50%, at least 55%, at least 60%, at least 65%, at least 70%, at least 75%, at least 80%, at least 85%, at least 90%, at least 95%, or at least 98% identical with amino acid residues 142-285 of a human BAFF protein that appears in Table 3. In some certain embodiments, said human nucleotide sequence encodes amino acid residues 142-285 of a human BAFF protein that are 100% identical with amino acid residues 142-285 of a human BAFF protein that appears in Table 3.

In some embodiments, the present invention provides a mouse or a rat made by, or obtained (or obtainable) from, a method as described herein. In some certain embodiments, a mouse or a rat made by, or obtained (or obtainable) from, a method as described herein does not detectably express a full-length endogenous (e.g., mouse or rat) Baff protein.

In some embodiments, the present invention provides a method of providing a mouse whose genome includes a Baff gene that encodes the extracellular portion of a human BAFF protein linked to the intracellular portion of a mouse Baff protein, the method comprising modifying the genome of a mouse so that it comprises a Baff gene that encodes the extracellular portion of a human BAFF protein linked to the intracellular portion of a mouse Baff protein thereby providing said mouse. In some embodiments, a Baff gene is a Baff gene as described herein. In some embodiments, a Baff gene is one that encodes a protein whose sequence reflects a humanized Baff protein that appears in Table 3. In some certain embodiments, a Baff gene comprises exons 3 to 6 a human BAFF gene.

In various embodiments, a humanized Baff gene of the present invention comprises exons 3, 4, 5 and 6 of a human BAFF gene. In various embodiments, an extracellular portion of a humanized Baff protein of the present invention comprises amino acids corresponding to residues 142-285 of a human BAFF protein that appears in Table 3. In some certain embodiments, a humanized Baff protein of the present invention comprises a sequence of a humanized Baff protein that appears in Table 3. In various embodiments, a humanized Baff gene of the present invention is operably linked to a mouse Baff promoter.

In some embodiments, the present invention provides a method of engrafting human cells into a mouse, the method comprising steps of providing a mouse whose genome comprises a Baff gene that encodes the extracellular portion of a human BAFF protein linked to the intracellular portion of a mouse Baff protein (as described herein), and transplanting one or more human cells into the mouse. In some certain embodiments, the method further comprises a step of assaying engraftment of the one or more human cells in the mouse. In some certain embodiments, the step of assaying comprises comparing the engraftment of the one or more human cells to the engraftment in one or more wild-type mice or in one or more mice whose genome does not comprise a Baff gene that encodes the extracellular portion of a human BAFF protein linked to the intracellular portion of a mouse Baff protein.

In some certain embodiments, the human cells are hematopoietic stem cells. In some certain embodiments, the human cells are human B cells.

In some embodiments, the human cells are transplanted intravenously. In some embodiments, the human cells are transplanted intraperitoneally. In some embodiments, the human cells are transplanted subcutaneously.

In some embodiments, the present invention provides methods for identification or validation of a drug or vaccine, the method comprising the steps of delivering a drug or vaccine to a non-human animal as described herein, and monitoring one or more of the immune response to the drug or vaccine, the safety profile of the drug or vaccine, or the effect on a disease or condition. In some embodiments, monitoring the safety profile includes determining if the non-human animal exhibits a side effect or adverse reaction as a result of delivering the drug or vaccine. In some embodiments, a side effect or adverse reaction is selected from morbidity, mortality, alteration in body weight, alteration of the level of one or more enzymes (e.g., liver), alteration in the weight of one or more organs, loss of function (e.g., sensory, motor, organ, etc.), increased susceptibility to one or more diseases, alterations to the genome of the non-human animal, increase or decrease in food consumption and complications of one or more diseases.

In some embodiments, the present invention provides use of a non-human animal of the present invention in the development of a drug or vaccine for use in medicine, such as use as a medicament.

In various embodiments, non-human animals of the present invention are rodents, preferably a mouse or a rat.

As used in this application, the terms "about" and "approximately" are used as equivalents. Any numerals used in this application with or without about; approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWING

The Drawing included herein, which is comprised of the following Figures, is for illustration purposes only not for limitation.

DEFINITIONS

Figure 1:
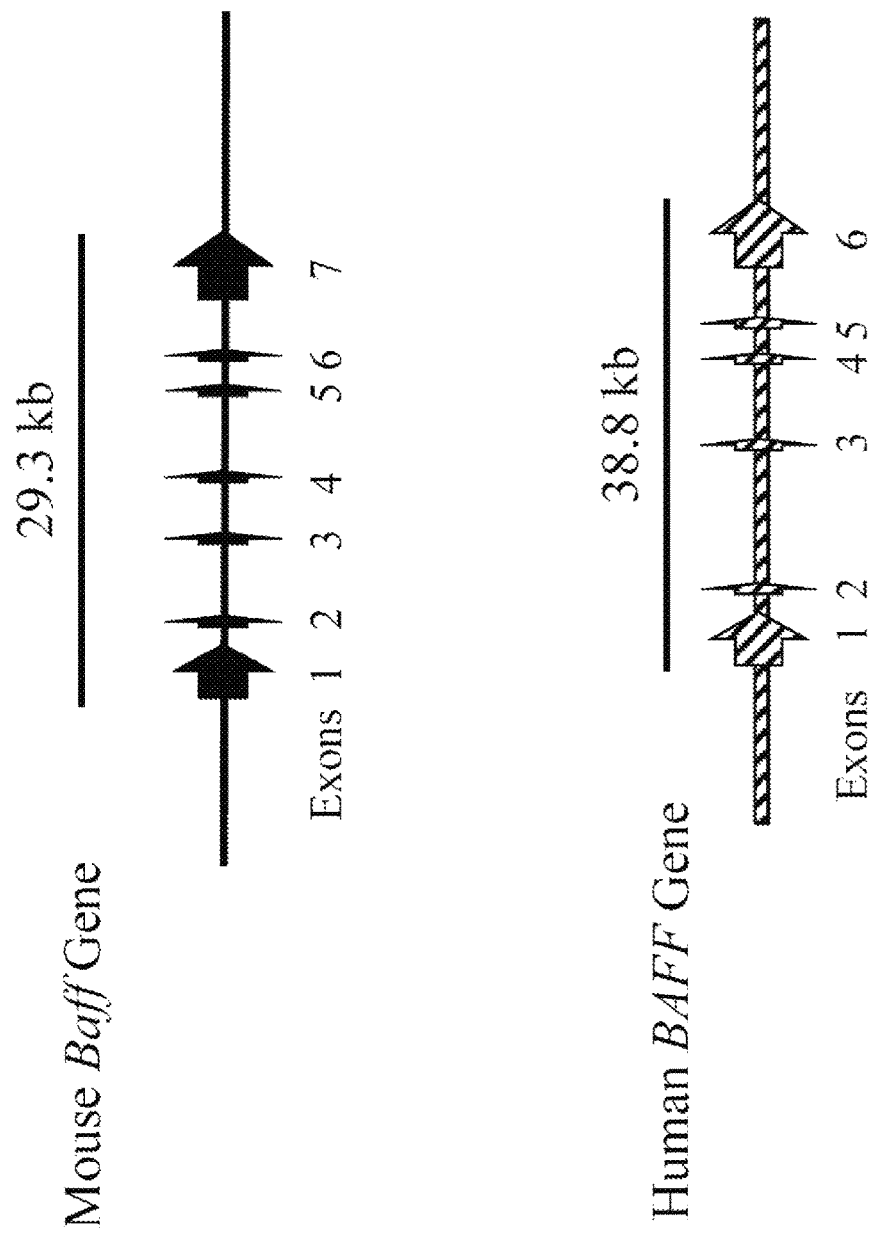
FIG. 1 shows a diagram, not to scale, of the genomic organization of mouse and human B-cell Activating Factor (BAFF) genes. Exons are numbered beneath each exon.

This invention is not limited to particular methods, and experimental conditions described, as such methods and conditions may vary. It is also to be understood that the terminology used herein is for the purpose of describing particular embodiments only, and is not intended to be limiting, since the scope of the present invention is defined by the claims.

Unless defined otherwise, all terms and phrases used herein include the meanings that the terms and phrases have attained in the art, unless the contrary is clearly indicated or clearly apparent from the context in which the term or phrase is used. Although any methods and materials similar or equivalent to those described herein can be used in the practice or testing of the present invention, particular methods and materials are now described. All publications mentioned are hereby incorporated by reference.

The term "approximately" as applied herein to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

The term "biologically active" as used herein refers to a characteristic of any agent that has activity in a biological system, in vitro or in vivo (e.g., in an organism). For instance, an agent that, when present in an organism, has a biological effect within that organism, is considered to be biologically active. In particular embodiments, where a protein or polypeptide is biologically active, a portion of that protein or polypeptide that shares at least one biological activity of the protein or polypeptide is typically referred to as a "biologically active" portion.

The term "comparable", as used herein, refers to two or more agents, entities, situations, sets of conditions, etc. that may not be identical to one another but that are sufficiently similar to permit comparison there between so that conclusions may reasonably be drawn based on differences or similarities observed. Those of ordinary skill in the art will understand, in context, what degree of identity is required in any given circumstance for two or more such agents, entities, situations, sets of conditions, etc. to be considered comparable.

The term "conservative" as used herein to describe a conservative amino acid substitution refers to substitution of an amino acid residue by another amino acid residue having a side chain R group with similar chemical properties (e.g., charge or hydrophobicity). In general, a conservative amino acid substitution will not substantially change the functional properties of interest of a protein, for example, the ability of a receptor to bind to a ligand. Examples of groups of amino acids that have side chains with similar chemical properties include aliphatic side chains such as glycine, alanine, valine, leucine, and isoleucine; aliphatic-hydroxyl side chains such as serine and threonine; amide-containing side chains such as asparagine and glutamine; aromatic side chains such as phenylalanine, tyrosine, and tryptophan; basic side chains such as lysine, arginine, and histidine; acidic side chains such as aspartic acid and glutamic acid; and, sulfur-containing side chains such as cysteine and methionine. Conservative amino acids substitution groups include, for example, valine/leucine/isoleucine, phenylalanine/tyrosine, lysine/arginine, alanine/valine, glutamate/aspartate, and asparagine/glutamine. In some embodiments, a conservative amino acid substitution can be substitution of any native residue in a protein with alanine, as used in, for example, alanine scanning mutagenesis. In some embodiments, a conservative substitution is one that that has a positive value in the PAM250 log-likelihood matrix disclosed in Gonnet et al. (1992) Exhaustive Matching of the Entire Protein Sequence Database, Science 256:1443-45, hereby incorporated by reference. In some embodiments, a substitution is deemed to be "moderately conservative" if it has a nonnegative value in the PAM250 log-likelihood matrix.

The term "disruption" as used herein refers to the result of an event that interrupts (e.g., via homologous recombination) a DNA. In some embodiments, a disruption may achieve or represent a deletion, insertion, inversion, modification, replacement, substitution, or any combination thereof, of a DNA sequence(s). In some embodiments, a disruption may achieve or represent introduction of a mutation, such as a missense, nonsense, or frame-shift mutation, or any combination thereof, in a coding sequence(s) in DNA. In some embodiments, a disruption may occur in a gene or gene locus endogenous to a cell. In some embodiments, insertions may include the insertion of entire genes or fragments of genes, e.g. exons, in to an endogenous site in a cell or genome. In some embodiments, insertions may introduce sequences that are of an origin other than that of an endogenous sequence into which they are inserted. In some embodiments, a disruption may increase expression and/or activity of a gene or gene product (e.g., of a protein encoded by a gene). In some embodiments, a disruption may decrease expression and/or activity of a gene or gene product. In some embodiments, a disruption may alter sequence of a gene or gene product (e.g., an encoded protein). In some embodiments, a disruption may truncate or fragment a gene or gene product (e.g., an encoded protein). In some embodiments, a disruption may extend a gene or gene product; in some such embodiments, a disruption may achieve assembly of a fusion protein. In some embodiments, a disruption may affect level but not activity of a gene or gene product. In some embodiments, a disruption may affect activity but not level of a gene or gene product. In some embodiments, a disruption may have no significant effect on level of a gene or gene product. In some embodiments, a disruption may have no significant effect on activity of a gene or gene product. In some embodiments, a disruption may have no significant effect on either level or activity of a gene or gene product.

The phrase "endogenous locus" or "endogenous gene" as used herein refers to a genetic locus found in a parent or reference organism prior to introduction of a disruption (e.g., deletion, insertion, inversion, modification, replacement, substitution, or a combination thereof as described herein). In some embodiments, an endogenous locus has a sequence found in nature. In some embodiments, an endogenous locus is wild type. In some embodiments, a reference organism that contains an endogenous locus as described herein is a wild-type organism. In some embodiments, a reference organism that contains an endogenous locus as described herein is an engineered organism. In some embodiments, a reference organism that contains an endogenous locus as described herein is a laboratory-bred organism (whether wild-type or engineered).

The phrase "endogenous promoter" refers to a promoter that is naturally associated, e.g., in a wild-type organism, with an endogenous gene.

The term "heterologous" as used herein refers to an agent or entity from a different source. For example, when used in reference to a polypeptide, gene, or gene product or present in a particular cell or organism, the term clarifies that the relevant polypeptide, gene, or gene product 1) was engineered by the hand of man; 2) was introduced into the cell or organism (or a precursor thereof) through the hand of man (e.g., via genetic engineering); and/or 3) is not naturally produced by or present in the relevant cell or organism (e.g., the relevant cell type or organism type).

The term "host cell", as used herein, refers to a cell into which a heterologous (e.g., exogenous) nucleic acid or protein has been introduced. Persons of skill upon reading this disclosure will understand that such terms refer not only to a particular subject cell, but also is used to refer to progeny of that cell. Because certain modifications may occur in succeeding generations due to either mutation or environmental influences, such progeny may not, in fact, be identical to the parent cell, but are still understood by those skilled in the art to be included within the scope of the term "host cell" as used herein. In some embodiments, a host cell is or comprises a prokaryotic or eukaryotic cell. In general, a host cell is any cell that is suitable for receiving and/or producing a heterologous nucleic acid or protein, regardless of the Kingdom of life to which the cell is designated. Exemplary cells that may be utilized as host cells in accordance with the present disclosure include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g., a retinal cell that expresses a viral gene (e.g., a PER.C6™ cell). In some embodiments, a host cell is or comprises an isolated cell. In some embodiments, a host cell is part of a tissue. In some embodiments, a host cell is part of an organism.

The term "humanized", is used herein in accordance with its art-understood meaning to refer to nucleic acids or proteins whose structures (i.e., nucleotide or amino acid sequences) include portions that correspond substantially or identically with versions of the relevant nucleic acids or proteins that are found in nature in non-human animals and that are distinguishable from corresponding versions that are found in nature in humans, and also include portions whose structures differ from those present in the non-human-animal versions and instead correspond more closely with comparable structures found in the human versions. In some embodiments, a "humanized" gene is one that encodes a polypeptide having substantially the amino acid sequence as that of a human polypeptide (e.g., a human protein or portion thereof—e.g., characteristic portion thereof). To give but one example, in the case of a membrane receptor, a "humanized" gene may encode a polypeptide with an extracellular portion whose amino acid sequence is identical or substantially identical to that of a human extracellular portion, and whose remaining sequence is identical or substantially identical to that of a non-human (e.g., mouse) polypeptide. In some embodiments, a humanized gene comprises at least a portion of an DNA sequence of a human gene. In some embodiment, a humanized gene comprises an entire DNA sequence found in a human gene. In some embodiments, a humanized protein has an amino acid sequence that comprises a portion that appears in a human protein. In some embodiments, a humanized protein has an amino acid sequence whose entire sequence is found in a human protein. In some embodiments (including, for example, some in which a humanized protein has an amino acid sequence whose entire sequence is found in a human protein), a humanized protein is expressed from an endogenous locus of a non-human animal, which endogenous locus corresponds to the homolog or ortholog of the relevant human gene encoding the protein.

The term "identity" as used herein in connection with a comparison of sequences, refers to identity as determined by any of a number of different algorithms known in the art that can be used to measure nucleotide and/or amino acid sequence identity. In some embodiments, identities as described herein are determined using a ClustalW v. 1.83 (slow) alignment employing an open gap penalty of 10.0, an extend gap penalty of 0.1, and using a Gonnet similarity matrix (MACVECTOR™ 10.0.2, MacVector Inc., 2008). As used herein, the term "identity" refers to the overall relatedness between polymeric molecules, e.g., between nucleic acid molecules (e.g., DNA molecules and/or RNA molecules) and/or between polypeptide molecules. In some embodiments, polymeric molecules are considered to be "substantially identical" to one another if their sequences are at least 25%, 30%, 35%, 40%, 45%, 50%, 55%, 60%, 65%, 70%, 75%, 80%, 85%, 90%, 95%, or 99% identical. As will be understood by those skilled in the art, a variety of algorithms are available that permit comparison of sequences in order to determine their degree of homology, including by permitting gaps of designated length in one sequence relative to another when considering which residues "correspond" to one another in different sequences. Calculation of the percent identity between two nucleic acid sequences, for example, can be performed by aligning the two sequences for optimal comparison purposes (e.g., gaps can be introduced in one or both of a first and a second nucleic acid sequences for optimal alignment and non-corresponding sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. Representative algorithms and computer programs useful in determining the percent identity between two nucleotide sequences include, for example, the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent identity between two nucleotide sequences can, alternatively, be determined for example using the GAP program in the GCG software package using an NWSgapdna.CMP matrix.

The term "isolated", as used herein, refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components a) with which it is associated in nature; and/or h) with which it was associated when initially produced.

The phrase "non-human animal" as used herein refers to a vertebrate organism that is not a human. In some embodiments, a non-human animal is a cyclostome, a bony fish, a cartilaginous fish (e.g., a shark or a ray), an amphibian, a reptile, a mammal, or a bird. In some embodiments, a non-human mammal is a primate, a goat, a sheep, a pig, a dog, a cow, or a rodent. In some embodiments, a non-human animal is a rodent such as a rat or a mouse.

The phrase "nucleic acid", as used herein, in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to one or more individual nucleic acid residues (e.g., nucleotides and/or nucleosides); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more analogs of a natural nucleic acid residue. In some embodiments, a nucleic acid analog differs from a natural nucleic acid residue in that it does not utilize a phosphodiester backbone. For example, in some embodiments, a nucleic acid is, comprises, or consists of one or more "peptide nucleic acids", which are known in the art and have peptide bonds instead of phosphodiester bonds in the backbone, are considered within the scope of the present invention. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxyguanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 2-thiocytidine, methylated bases, intercalated bases, and combinations thereof). In some embodiments, a nucleic acid comprises one or more modified sugars (e.g., 2'-fluororibose, ribose, 2'-deoxyribose, arabinose, and hexose) as compared with those in natural nucleic acids (i.e., comprises one or more analogs of a natural nucleoside sugar). In some embodiments, a nucleic acid has a nucleotide sequence that encodes a functional gene product such as an RNA or protein. In some embodiments, a nucleic acid has a nucleotide sequence that includes one or more introns. Those of ordinary skill in the art will appreciate that a variety of technologies are available and known in the art for the production of nucleic acids. For example, in some embodiments, nucleic acids are prepared by a method selected from the group consisting of isolation from a natural source, enzymatic synthesis by polymerization based on a complementary template (in vivo or in vitro), reproduction in a recombinant cell or system, chemical synthesis, and combinations thereof. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a nucleic acid is single stranded; in some embodiments, a nucleic acid is partially or fully double stranded (i.e., comprises at least two individual nucleic acid strands whose sequences include complementary elements that hybridize to one another). In some embodiments a nucleic acid has a nucleotide sequence comprising at least one element that encodes, or is the complement of a sequence that encodes, a polypeptide. In some embodiments, a nucleic acid has enzymatic activity.

1541 The phrase "operably linked", as used herein, refers to a physical juxtaposition (e.g., in three-dimensional space) of components or elements that interact, directly or indirectly with one another, or otherwise coordinate with each other to participate in a biological event, which juxtaposition achieves or permits such interaction and/or coordination. To give but one example. A control sequence (e.g., an expression control sequence) in a nucleic acid is said to be "operably linked" to a coding sequence when it is located relative to the coding sequence such that its presence or absence impacts expression and/or activity of the coding sequence. In many embodiments, "operable linkage" involves covalent linkage of relevant components or elements with one another. Those skilled in the art will readily appreciate, however, that in some embodiments, covalent linkage is not required to achieve effective operable linkage. For example, in some embodiments, nucleic acid control sequences that are operably linked with coding sequences that they control are contiguous with the gene of interest. Alternatively or additionally, in some embodiments, one or more such control sequences acts in trans or at a distance to control a coding sequence of interest. In some embodiments, the term "expression control sequence" as used herein refers to polynucleotide sequences which are necessary and/or sufficient to effect the expression and processing of coding sequences to which they are ligated. In some embodiments, expression control sequences may be or comprise appropriate transcription initiation, termination, promoter and/or enhancer sequences; efficient RNA processing signals such as splicing and polyadenylation signals; sequences that stabilize cytoplasmic mRNA; sequences that enhance translation efficiency (e.g., Kozak consensus sequence); sequences that enhance protein stability; and/or, in some embodiments, sequences that enhance protein secretion. In some embodiments, one or more control sequences is preferentially or exclusively active in a particular host cell or organism, or type thereof. To give but one example, in prokaryotes, control sequences typically include promoter, ribosomal binding site, and transcription termination sequence; in eukaryotes, in many embodiments, control sequences typically include promoters, enhancers, and/or transcription termination sequences. Those of ordinary skill in the art will appreciate from context that, in many embodiments, the term "control sequences" refers to components whose presence is essential for expression and processing, and in some embodiments includes components whose presence is advantageous for expression (including, for example, leader sequences, targeting sequences, and/or fusion partner sequences).

The term "polypeptide", as used herein, refers to any polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man.

The term "recombinant", as used herein, is intended to refer to polypeptides (e.g., B cell activating factor proteins as described herein) that are designed, engineered, prepared, expressed, created or isolated by recombinant means, such as polypeptides expressed using a recombinant expression vector transfected into a host cell, polypeptides isolated from a recombinant, combinatorial human polypeptide library (Hoogenboom H. R., (1997) TIB Tech. 15:62-70; Azzazy H., and Highsmith W. E., (2002) Clin. Biochem. 35:425-445; Gavilondo J. V., and Larrick J. W. (2002) BioTechniques 29:128-145; Hoogenboom H., and Chames P. (2000) Immunology Today 21:371-378), antibodies isolated from an animal (e.g., a mouse) that is transgenic for human immunoglobulin genes (see e.g., Taylor, L. D., et al. (1992) Nucl. Acids Res. 20:6287-6295; Kellermann S-A., and Green L. L. (2002) Current Opinion in Biotechnology 13:593-597; Little M. et al (2000) Immunology Today 21:364-370) or polypeptides prepared, expressed, created or isolated by any other means that involves splicing selected sequence elements to one another. In some embodiments, one or more of such selected sequence elements is found in nature. In some embodiments, one or more of such selected sequence elements is designed in silico. In some embodiments, one or more such selected sequence elements results from mutagenesis (e.g., in vivo or in vitro) of a known sequence element, e.g., from a natural or synthetic source. For example, in some embodiments, a recombinant polypeptide is comprised of sequences found in the genome of a source organism of interest (e.g., human, mouse, etc.). In some embodiments, a recombinant polypeptide has an amino acid sequence that resulted from mutagenesis (e.g., in vitro or in vivo, for example in a non-human animal), so that the amino acid sequences of the recombinant polypeptides are sequences that, while originating from and related to polypeptides sequences, may not naturally exist within the genome of a non-human animal in vivo.

The term "replacement" is used herein to refer to a process through which a "replaced" nucleic acid sequence (e.g., a gene) found in a host locus (e.g., in a genome) is removed from that locus and a different, "replacement" nucleic acid is located in its place. In some embodiments, the replaced nucleic acid sequence and the replacement nucleic acid sequences are comparable to one another in that, for example, they are homologous to one another and/or contain corresponding elements (e.g., protein-coding elements, regulatory elements, etc.). In some embodiments, a replaced nucleic acid sequence includes one or more of a promoter, an enhancer, a splice donor site, a splice receiver site, an intron, an exon, an untranslated region (UTR); in some embodiments, a replacement nucleic acid sequence includes one or more coding sequences. In some embodiments, a replacement nucleic acid sequence is a homolog of the replaced nucleic acid sequence. In some embodiments, a replacement nucleic acid sequence is an ortholog of the replaced sequence. In some embodiments, a replacement nucleic acid sequence is or comprises a human nucleic acid sequence. In some embodiments, including where the replacement nucleic acid sequence is or comprises a human nucleic acid sequence, the replaced nucleic acid sequence is or comprises a rodent sequence (e.g., a mouse sequence). The nucleic acid sequence so placed may include one or more regulatory sequences that are part of source nucleic acid sequence used to obtain the sequence so placed (e.g., promoters, enhancers, 5'- or 3'-untranslated regions, etc.). For example, in various embodiments, the replacement is a substitution of an endogenous sequence with a heterologous sequence that results in the production of a gene product from the nucleic acid sequence so placed (comprising the heterologous sequence), but not expression of the endogenous sequence; the replacement is of an endogenous genomic sequence with a nucleic acid sequence that encodes a protein that has a similar function as a protein encoded by the endogenous sequence (e.g., the endogenous genomic sequence encodes a Baff protein, and the DNA fragment encodes one or more human BAFF proteins). In various embodiments, an endogenous gene or fragment thereof is replaced with a corresponding human gene or fragment thereof. A corresponding human gene or fragment thereof is a human gene or fragment that is an ortholog of, or is substantially similar or the same in structure and/or function, as the endogenous gene or fragment thereof that is replaced.

The phrase "B-cell activating factor" or "BAFF" or "Baff" as used herein refers to a tumor necrosis family ligand, e.g., a TNF family ligand. BAFF is a type II membrane-bound protein, which can be released as a soluble ligand upon proteolytic processing at a furin cleavage site. BAFF proteins can form multimers (e.g., timers) depending on pH conditions. This characteristic is may be important for receptor binding. BAFF is expressed on the surface of a cell and serves as a regulatory protein involved in interactions between membrane surface proteins on immune cells, e.g., B cells. Several variants, including those resulting from alternative splicing events, have been described in human subjects as well as in rodents. By way of illustration, nucleotide and amino acid sequences of mouse and human BAFF genes are provided in Table 3. Persons of skill upon reading this disclosure will recognize that one or more endogenous Baff genes in a genome (or all) can be replaced by one or more heterologous Baff genes (e.g., polymorphic variants, subtypes or mutants, genes from another species, humanized forms, etc.).

A "BAFF-expressing cell" as used herein refers to a cell that expresses a B-cell activating factor ligand. In some embodiments, a BAFF-expressing cell expresses a B-cell activating factor ligand on its surface. In some embodiments, a BAFF protein is expressed on the surface of the cell in an amount sufficient to mediate cell-to-cell interactions via the BAFF protein expressed on the surface of the cell. In some embodiments, a BAFF-expressing cell express a B-cell activating factor ligand in soluble form (i.e., not on the surface of a cell). Exemplary BAFF-expressing cells include, but are not limited to, astrocytes, dendritic cells, monocytes, neutrophils and stromal cells. BAFF interacts with receptors found predominantly on B cell lineages and is involved in the activation and survival of B cells. In some embodiments, non-human animals of the present invention demonstrate immune cell regulation via humanized Baff ligands expressed on the surface of one more cells of the non-human animal. In some embodiments, non-human animals of the present invention promote the long-term survival of B cells in non-human animals that comprise heterologous hematopoietic stem cells (e.g., human). In some embodiments, non-human animals of the present invention promote the long-term survival of antigen-specific B cells in non-human animals that comprise heterologous hematopoietic stem cells (e.g., human).

The term "substantially" as used herein refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

The phrase "substantial homology" as used herein refers to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains. Substitution of one amino acid for another of the same type may often be considered a "homologous" substitution. Typical amino acid categorizations are summarized in Table 1 and 2.

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul, et al., "Gapped BLAST and PSI-BLAST: a new generation of protein database search programs", *Nucleic Acids Res.* 25:3389-3402, 1997; Baxevanis, et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 9, 10, 11, 12, 13, 14, 15, 16, 17 or more residues. In some embodiments, the relevant stretch includes contiguous residues along a complete sequence. In some embodiments, the relevant stretch includes discontinuous residues along a complete sequence. In some embodiments, the relevant stretch is at least 10, 15, 20, 25, 30, 35, 40, 45, 50, or more residues.

TABLE 1

| Alanine | Ala | A | nonpolar | neutral | 1.8 |
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | nonpolar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

TABLE 2

| Ambiguous Amino Acids | 3-Letter | 1-Letter |
|---|---|---|
| Asparagine or aspartic acid | Asx | B |
| Glutamine or glutamic acid | Glx | Z |

TABLE 2-continued

| Ambiguous Amino Acids | 3-Letter | 1-Letter |
|---|---|---|
| Leucine or Isoleucine | Xle | J |
| Unspecified or unknown amino acid | Xaa | X |

The phrase "substantial identity" as used herein refers to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul et al., *Nucleic Acids Res.* 25:3389-3402, 1997; Baxevanis et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, or more residues.

The phrase "targeting vector" or "targeting construct" as used herein refers to a polynucleotide molecule that comprises a targeting region. A targeting region comprises a sequence that is identical or substantially identical to a sequence in a target cell, tissue or animal and provides for integration of the targeting construct into a position within the genome of the cell, tissue or animal via homologous recombination. Targeting regions that target using site-specific recombinase recognition sites (e.g., LoxP or Frt sites) are also included. In some embodiments, a targeting construct of the present invention further comprises a nucleic acid sequence or gene of particular interest, a selectable marker, control and or regulatory sequences, and other nucleic acid sequences that allow for recombination mediated through exogenous addition of proteins that aid in or facilitate recombination involving such sequences. In some embodiments, a targeting construct of the present invention further comprises a gene of interest in whole or in part, wherein the gene of interest is a heterologous gene that encodes a protein in whole or in part that has a similar function as a protein encoded by an endogenous sequence.

The term "variant", as used herein, refers to an entity that shows significant structural identity with a reference entity but differs structurally from the reference entity in the presence or level of one or more chemical moieties as compared with the reference entity. In many embodiments, a variant also differs functionally from its reference entity. In general, whether a particular entity is properly considered to be a "variant" of a reference entity is based on its degree of structural identity with the reference entity. As will be appreciated by those skilled in the art, any biological or chemical reference entity has certain characteristic structural elements. A variant, by definition, is a distinct chemical entity that shares one or more such characteristic structural elements. To give but a few examples, a small molecule may have a characteristic core structural element (e.g., a macrocycle core) and/or one or more characteristic pendent moieties so that a variant of the small molecule is one that shares the core structural element and the characteristic pendent moieties but differs in other pendent moieties and/or in types of bonds present (single vs. double, E vs. Z, etc.) within the core, a polypeptide may have a characteristic sequence element comprised of a plurality of amino acids having designated positions relative to one another in linear or three-dimensional space and/or contributing to a particular biological function, a nucleic acid may have a characteristic sequence element comprised of a plurality of nucleotide residues having designated positions relative to on another in linear or three-dimensional space. For example, a variant polypeptide may differ from a reference polypeptide as a result of one or more differences in amino acid sequence and/or one or more differences in chemical moieties (e.g., carbohydrates, lipids, etc.) covalently attached to the polypeptide backbone. In some embodiments, a variant polypeptide shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a variant polypeptide does not share at least one characteristic sequence element with a reference polypeptide. In some embodiments, the reference polypeptide has one or more biological activities. In some embodiments, a variant polypeptide shares one or more of the biological activities of the reference polypeptide. In some embodiments, a variant polypeptide lacks one or more of the biological activities of the reference polypeptide. In some embodiments, a variant polypeptide shows a reduced level of one or more biological activities as compared with the reference polypeptide. In many embodiments, a polypeptide of interest is considered to be a "variant" of a parent or reference polypeptide if the polypeptide of interest has an amino acid sequence that is identical to that of the parent but for a small number of sequence alterations at particular positions. Typically, fewer than 20%, 15%, 10%, 9%, 8%, 7%, 6%, 5%, 4%, 3%, 2% of the residues in the variant are substituted as compared with the parent. In some embodiments, a variant has 10, 9, 8, 7, 6, 5, 4, 3, 2, or 1 substituted residue as compared with a parent. Often, a variant has a very small number (e.g., fewer than 5, 4, 3, 2, or 1) number of substituted functional residues (i.e., residues that participate in a particular biological activity). Furthermore, a variant typically has not more than 5, 4, 3, 2, or 1 additions or deletions, and often has no additions or deletions, as compared with the parent. Moreover, any additions or deletions are typically fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, the parent or reference polypeptide is one found in nature. As will be understood by those of ordinary skill in the art, a plurality of variants of a particular polypeptide of interest may commonly be found in nature, particularly when the polypeptide of interest is an infectious agent polypeptide.

The term "vector", as used herein, refers to a nucleic acid molecule capable of transporting another nucleic acid to which it is associated. In some embodiment, vectors are capable of extra-chromosomal replication and/or expression of nucleic acids to which they are linked in a host cell such as a eukaryotic and/or prokaryotic cell. Vectors capable of directing the expression of operatively linked genes are referred to herein as "expression vectors."

The term "wild-type", as used herein, has its art-understood meaning that refers to an entity having a structure and/or activity as found in nature in a "normal" (as contrasted with mutant, diseased, altered, etc.) state or context. Those of ordinary skill in the art will appreciate that wild type genes and polypeptides often exist in multiple different forms (e.g., alleles).

DETAILED DESCRIPTION OF CERTAIN EMBODIMENTS

The present invention provides, among other things, improved and/or engineered non-human animals having humanized genetic material encoding a B-cell activating factor protein (e.g., Baff). In certain embodiments, such non-human animals are useful, for example, for assays in transplant engraftment, B cell activation and survival of antigen-specific B cells post immunization. It is contemplated that such non-human animals provide an improvement in B cell activation and survival of antigen-specific B cells post immunization post-engraftment of human hematopoietic stem cells. Therefore, the present invention is particularly useful for maintaining human hematopoietic cells in non-human animals. In particular, the present invention encompasses the humanization of a rodent Baff gene resulting in expression of a humanized protein on the plasma membrane surface of cells of the non-human animal. Such humanized proteins have the capacity to recognize engrafted human cells via engagement of humanized Baff proteins and ligands/receptors present on the surface of the engrafted human cells. In some embodiments, non-human animals of the present invention are capable of receiving transplanted human hematopoietic cells; in some embodiments, such non-human mammals develop and/or have an immune system comprising human cells. In some embodiments, humanized Baff proteins have sequence encoded by exons 3 to 6 of a human BAFF gene. In some embodiments, non-human animals of the present invention comprise a genetically modified Baff gene that contains genetic material from the non-human animal and a heterologous species (e.g., a human). In some embodiments, non-human animals of the present invention comprise a humanized Baff gene, wherein the humanized Baff gene comprises exons 3, 4, 5 and 6 of a human BAFF gene. In some embodiments, the expression of the humanized Baff protein is under the control of non-human Baff genetic material (e.g., a non-human Baff promoter).

Various aspects of the invention are described in detail in the following sections. The use of sections is not meant to limit the invention. Each section can apply to any aspect of the invention. In this application, the use of "or" means "and/or" unless stated otherwise.

B-Cell Activating Factor (BAFF) Gene

B-cell activating factor (BAFF or Baff) is a member of the tumor necrosis factor (TNF) ligand superfamily and is expressed by many different cell types including, but not limited to, astrocytes, B cell lineage cells, dendritic cells, monocytes, neutrophils and stromal cells. BAFF (also referred to as tumor necrosis factor ligand superfamily member 13C, TNFSF13C, BAFF, BLYS, CD257, DTL, TALL-1, TALL-1, THANK, TNFSF20 and ZTNF4) is expressed on the cell surface as a Type II transmembrane protein and can be released in soluble form via cleavage at a furin consensus site after proteolysis. Soluble BAFF can exist in multiple forms (e.g., timers, 60-mers) depending upon pH. The gene structure for BAFF in mouse and man differ slightly in that the former contains an additional exon. In humans, exon 1 encodes the transmembrane domain, exon 2 encodes the furin cleavage site, and exons 3 to 6 encode the TNF domain, which is responsible for receptor binding. In mouse, exon 1 encodes the transmembrane domain, exon 2 encodes the furin cleavage site, exon 3 encodes additional amino acids between the furin site and the TNF domain, and exons 4-7 encode the TNF domain. For both mouse and man, alternative splice variants result in a deletion of an interior portion of the protein which yield a variant referred to as "delta-BAFF" (or ΔBAFF). In humans, it is exon 3 that is skipped, whereas in mouse it is exon 4 that is skipped. ΔBAFF is still expressed on the cell surface, however, release of the soluble form is reportedly prevented.

Reported receptors for BAFF include, most notably, BAFF receptor (BAFF-R), but also include transmembrane activator and calcium modulator and cyclophilin ligand interactor (TACI) and B cell maturation antigen (BCMA). BAFF binds to both BAFF-R and TACI with strong affinity, whereas BAFF binds to BCMA with weak affinity.

The role of Baff, in particular, has been investigated in respect of its role in the activation and differentiation of B cells. For example, elevated levels of Baff in transgenic mice overexpressing mouse Baff were found to promote the survival, tolerance and rescue of B cells with affinity for self-antigens thereby promoting autoantibody secretion (Ota et al., 2010, J. Immunol. 185:4128-4136).

BAFF Sequences

Exemplary BAFF sequences for human and mouse are set forth in Table 3. For cDNA sequences, consecutive exons are separated by alternating underlined text. For protein sequences, predicted transmembrane regions are underlined.

TABLE 3

| | |
|---|---|
| Mouse Baff cDNA NM_033622.1 | GGCACGAGGCAGATTGAGCAATCCATGGAAGGCCAGAGCCAGAGAA CCTACTTCAGGGTAGCAAAAGATGCAGAAGAAAGTCAGGAGAGCGC TCCTGGGGGAACCCAGCCCTGCCATGCTCTGAGGGCAGTCTCCCAG GACACAGATGACAGGAAATGACCCACCCCTGTGGTCACTTACTCCA AAGGCCTAGACCTTCAAAGTGCTCCTCGTGGAATGGATGAGTCTGC AAAGACCCTGCCACCACCGTGCCTCTGTTTTTGCTCCGAGAAAGGA GAAGATATGAAAGTGGGATATGATCCCATCACTCCGCAGAAGGAGG AGGGTGCCTGGTTTGGGATCTGCAGGGATGGAAGGCTGCTGGCTGC TACCCTCCTGCTGGCCCTGTTGTCCAGCAGTTTCACAGCGATGTCC TTGTACCAGTTGGCTGCCTTGCAAGCAGACCTGATGAACCTGCGCA TGGAGCTGCAGAGCTACCGAGGTTCAGCAACACCAGCCGCCGCGGG TGCTCCAGAGTTGACCGCTGGAGTCAAACTCCTGACACCGGCAGCT CCTCGACCCCACAACTCCAGCCGCGGCCACAGGAACAGACGCGCTT TCCAGGGACCGAGGGAAACAGAACAAGATGTAGACCTCTCAGCTCC TCCTGCACCATGCCTGCCTGGATGCCGCCATTCTCAACATGATGAT AATGGAATGAACCTCAGAAACATCATTCAAGACTGTCTGCAGCTGA TTGCAGACAGCGACACGCCGACTATACGAAAAGGAACTTACACATT TGTTCCATGGCTTCTCAGCTTTAAAAGAGGAAATGCCTTGGAGGAG AAAGAGAACAAAATAGTGGTGAGGCAAACAGGCTATTTCTTCATCT ACAGCCAGGTTCTATACACGGACCCCATCTTTGCTATGGGTCATGT CATCCAGAGGAAGAAAGTACACGTCTTTGGGGACGAGCTGAGCCTG GTGACCCTGTTCCGATGTATTCAGAATATGCCCAAAACACTGCCCA ACAATTCCTGCTACTCGGCTGGCATCGCGAGGCTGGAAGAAGGAGA TGAGATTCAGCTTGCAATTCCTCGGGAGAATGCACAGATTTCACGC AACGGAGACGACACCTTCTTTGGTGCCCTAAAACTGCTGTAACTCA CTTGCTGGAGTGCGTGATCCCCTTCCCTCGTCTTCTCTGTACCTCC GAGGGAGAAACAGACGACTGGAAAAACTAAAAGATGGGGAAAGCCG TCAGCGAAAGTTTTCTCGTGACCCGTTGAATCTGATCCAAACCAGG AAATATAACAGACAGCCACAACCGAAGTGTGCCATGTGAGTTATGA GAAACGGAGCCCGCGCTCAGAAAGACCGGATGAGGAAGACCGTTTT CTCCAGTCCTTTGCCAACACGCACCGCAACCTTGCTTTTTGCCTTG GGTGACACATGTTCAGAATGCAGGGAGATTTCCTTGTTTTGCGATT TGCCATGAGAAGAGGGCCCACAACTGCAGGTCACTGAAGCATTCAC GCTAAGTCTCAGGATTTACTCTCCCTTCTCATGCTAAGTACACACA CGCTCTTTTCCAGGTAATACTATGGGATACTATGGAAAGGTTGTTT GTTTTTAAATCTAGAAGTCTTGAACTGGCAATAGACAAAAATCCTT ATAAATTCAAGTGTAAAATAAACTTAATTAAAAAGGTTTAAGTGTG AAAAAAAA (SEQ ID NO: 1) |
| Mouse Baff Protein NP_296371.1 | MDESAKTLPPPCLCFCSEKGEDMKVGYDPITPQKEEGAWFGICRDG RLLAATLLLALLSSSFTAMSLYQLAALQADLMNLRMELQSYRGSAT PAAAGAPELTAGVKLLTPAAPRPHNSSRGHRNRRAFQGPEETEQDV DLSAPPAPCLPGCRHSQHDDNGMNLRNIIQDCLQLIADSDTPTIRK GTYTFVPWLLSFKRGNALEEKENKIVVRQTGYFFIYSQVLYTDPIF AMGHVIQRKKVHVFGDELSLVTLFRCIQNMPKTLPNNSCYSAGIAR LEEGDEIQLAIPRENAQISRNGDDTFFGALKLL (SEQ ID NO: 2) |
| Mouse ΔBaff Protein AY290823.1 | MDESAKTLPPPCLCFCSEKGEDMKVGYDPITPQKEEGAWFGICRDG RLLAATLLLALLSSSFTAMSLYQLAALQADLMNLRMELQSYRGSAT PAAAGAPELTAGVKLLTPAAPRPHNSSRGHRNRRAFQGPEETEQDV DLSAPPAPCLPGCRHSQHDDNGMNLRNRTYTFVPWLLSFKRGNALE EKENKIVVRQTGYFFIYSQVLYTDPIFAMGHVIQRKKVHVFGDELS LVTLFRCIQNMPKTLPNNSCYSAGIARLEEGDEIQLAIPRENAQIS RNGDDTFFGALKLL (SEQ ID NO: 3) |

TABLE 3-continued

| | |
|---|---|
| Human BAFF cDNA<br>NM_006573.4 | GAAATTCTTACAAAAACTGAAAGTGAAATGAGGAAGACAGATTGAG<br>CAATCCAATCGGAGGGTAAATGCCAGCAAACCTACTGTACAGTAGG<br>GGTAGAGATGCAGAAAGGCAGAAAGGAGAAAATTCAGGATAACTCT<br>CCTGAGGGGTGAGCCAAGCCCTGCCATGTAGTGCACGCAGGACATC<br>AACAAACACAGATAACAGGAAATGATCCATTCCCTGTGGTCACTTA<br>TTCTAAAGGCCCCAACCTTCAAAGTTCAAGTAGTGATATGGATGAC<br>TCCACAGAAAGGGAGCAGTCACGCCTTACTTCTTGCCTTAAGAAAA<br>GAGAAGAAATGAAACTGAAGGAGTGTGTTTCCATCCTCCCACGGAA<br>GGAAAGCCCCTCTGTCCGATCCTCCAAAGACGGAAAGCTGCTGGCT<br>GCAACCTTGCTGCTGGCACTGCTGTCTTGCTGCCTCACGGTGGTGT<br>CTTTCTACCAGGTGGCCGCCCTGCAAGGGGACCTGGCCAGCCTCCG<br>GGCAGAGCTGCAGGGCCACCACGCGGAGAAGCTGCCAGCAGGAGCA<br>GGAGCCCCCAAGGCCGGCCTGGAGGAAGCTCCAGCTGTCACCGCGG<br>GACTGAAAATCTTTGAACCACCAGCTCCAGGAGAAGGCAACTCCAG<br>TCAGAACAGCAGAAATAAGCGTGCCGTTCAGGGTCCAGAAGAAACA<br>GTCACTCAAGACTGCTTGCAACTCATTTGTTCCATGGCTTCTCAGCTT<br>CTATACAAAAGGATCTTACACATTTGTTCCATGGCTTCTCAGCTT<br>TAAAAGGGGAAGTGCCCTAGAAGAAAAAGAGAATAAAATATTGGTC<br>AAAGAAACTGGTTACTTTTTTATATATGGTCAGGTTTTATATACTG<br>ATAAGACCTACGCCATGGGACATCTAATTCAGAGGAAGAAGGTCCA<br>TGTCTTTGGGGATGAATTGAGTCTGGTGACTTTGTTTCGATGTATT<br>CAAAATATGCCTGAAACACTACCCAATAATTCCTGCTATTCAGCTG<br>GCATTGCAAAACTGGAAGAAGGAGATGAACTCCAACTTGCAATACC<br>AAGAGAAAATGCACAAATATCACTGGATGGAGATGTCACATTTTTT<br>GGTGCATTGAAACTGCTGTGACCTACTTACACCATGTCTGTAGCTA<br>TTTTCCTCCCTTTCTCTGTACCTCAAGAAGAAAGAATCTAACTGA<br>AAATACCAAAAAAAAAAAAAAAAAAAAAAAAAAAAAAAAGTAGTTAC<br>CATTGCCTTTTCTGTGAGCTATTTGTTTTGGTTTGCTGAAACTAGT<br>CCAAAACAGGAAATTTAACAGACAGCCACAGCCAAAGAGTGTCATG<br>TGAATTACAAGAATAGAGCCCATTTAGGGAAAGATAGAACTAGAA<br>AGGCTTTTCATTATAATTCCATGTGAACAATTGAGTCATAGCTTC<br>TTATCTTGGAGGAAGGACACAATTCAAAGGGGCAGTAAGGATTTTG<br>TAAAACGTGGCATCCATAATTTACTATGGAGCAAGTGCCCACATCT<br>CTAGGACATTAAGACATTTATGAGAAATCTCAGGATTCATCTTCTG<br>TTTTTATGTTAAATGCACTCCCTCCTTTTCAGTTAACATTATAAAA<br>AGTAAAAAATGAAAATTTTAGAAATCTTGCATTAGACACATGAAAA<br>AATAACTAAAAGTTTAAATTTAAATATGAAACAATTTTGCTGAAAA<br>TAGTATCCATATACTATTTAAGTCTTTTATGGTTATTTCAAGTATA<br>CAATTTCTATCTGTAATGTAATATATTACCCACACATTTTTTTCAC<br>AGGAGAGAGAGAATATCCTCATTTGTTTATGCTCATGTGTATTTC<br>TATAGTGAATTTCAGAAACTTTTAATATCAGGTAATTTCAATTTAT<br>GCCTATAAAGCATTGATTGAAAAATAACTAGAATTGTGCATATATA<br>ACACATAATCTCCAACAGAAGTTACTGAATACATTCATACTAATGT<br>AATGTAATTTCCCTTTATTTCTTGCTCTTCTGTTTCAAACTGCTGC<br>TATTGTAGTTTACATATCCCAACCTTTAAAAATATTCCTCTTATTA<br>GCTTTATATTCACTTTATAGAAGTTGAGTTTAATTAAAATTCTTG<br>GCATCCTGAAGTATGTCACATAGCATGTGCTCCTTATAAATATGTT<br>GATATCTCAGAAGACAGCATCCCGGTTTTCATTTTATAAAGTACCA<br>TACTTAAGAATGCTGTAATACTTATCTTTTATAACATGTTTCCTTC<br>GCTTTGCTTGTCTTTTATGTCATCAGTTTTAACTGTTTACTTCATT<br>TAACAGTTTACATCATTCAACAGTTTACTTCATTAAACAGTAGGTG<br>GAAAAATAGATGCCAGTCTATGAAAATCTTCCCATCTATATCAAAA<br>TACTTTTCAAGGATATACTTTTCAAAACAAACGATTTAAATTTTAT<br>GTTTAAAATATAAACTTTAGATTTAAACTTTATTTAAATATCTGGT<br>TCCTATGATTTTGACTTCAGTAAGTTCAAATAAAATATATTTTGCA<br>ATTCATTTTACATTATAATTTAAAAGAAGAAGCGATAAGTGGAG<br>TCAGTTTCAATGCTAGGTGGGGTGGTTAATGATTTTTCTGGTGTTG<br>CTGCTAATGTGGATTAACAAATAAAAACATTCATTGCCTTTTGCCT<br>CATAAAA (SEQ ID NO: 4) |
| Human BAFF Protein<br>NP_006564.1 | MDDSTEREQSRLTSCLKKREEMKLKECVSILPRKESPSVRSSKDGK<br>LLAATLLLALLSCCLTVVSFYQVAALQGDLASLRAELQGHHAEKLP<br>AGAGAPKAGLEEAPAVTAGLKIFEPPAPGEGNSSQNSRNKRAVQGP<br>EETVTQDCLQLIADSETPTIQKGSYTFVPWLLSFKRGSALEEKENK<br>ILVKETGYFFIYGQVLYTDKTYAMGHLIQRKKVHVFGDELSLVTLF<br>RCIQNMPETLPNNSCYSAGIAKLEEGDELQLAIPRENAQISLDGDV<br>TFFGALKLL (SEQ ID NO: 5) |
| Human ΔBAFF Protein<br>AY302751.1 | MDDSTEREQSRLTSCLKKREEMKLKECVSILPRKESPSVRSSKDGK<br>LLAATLLLALLSCCLTVVSFYQVAALQGDLASLRAELQGHHAEKLP<br>AGAGAPKAGLEEAPAVTAGLKIFEPPAPGEGNSSQNSRNKRAVQGP<br>EETGSYTFVPWLLSFKRGSALEEKENKILVKETGYFFIYGQVLYTD<br>KTYAMGHLIQRKKVHVFGDELSLVTLFRCIQNMPETLPNNSCYSAG<br>IAKLEEGDELQLAIPRENAQISLDGDVTFFGALKLL<br>(SEQ ID NO: 6) |
| Humanized Baff<br>Protein | MDESAKTLPPPCLCFCSEKGEDMKVGYDPITPQKEEGAWFGICRDG<br>RLLAATLLLALLSSSFTAMSLYQLAALQADLMNLRMELQSYRGSAT<br>PAAAGAPELTAGVKLLTPAAPRPHNSSRGHRNRRAFQGPEET*VTQD* |

TABLE 3-continued

```
CLQLIADSETPTIQKGSYTFVPWLLSFKRGSALEEKENKILVKETG
YFFIYGQVLYTDKTYAMGHLIQRKKVHVFGDELSLVTLFRCIQNMP
ETLPNNSCYSAGIAKLEEGDELQLAIPRENAQISLDGDVTFFGALK
LL (SEQ ID NO: 7)
```

Humanized Baff Non-Human Animals

Non-human animals are provided that express genetically modified (e.g., humanized) Baff proteins on the surface of cells (e.g., dendritic cells) of the non-human animals. Specifically, the present invention provides non-human animals that express genetically modified (e.g., humanized) Baff proteins on the surface of their cells, the proteins being encoded by and/or expressed from a genetic modification of an endogenous locus of the non-human animal that encodes a Baff protein. Suitable examples presented herein specifically exemplify rodents, in particular, mice.

A genetically modified Baff gene, in some embodiments, comprises genetic material from a heterologous species (e.g., humans), wherein the genetically modified Baff gene encodes a Baff protein that comprises the encoded portion of the genetic material from the heterologous species. In some embodiments, a genetically modified Baff gene of the present invention comprises genomic DNA of a heterologous species that corresponds to the extracellular portion of a Baff protein that is expressed on the plasma membrane of a cell. Non-human animals, embryos, cells and targeting constructs for making non-human animals, non-human embryos, and cells containing said genetically modified Baff gene are also provided.

In some embodiments, the endogenous Baff gene is deleted. In some embodiments, the endogenous Baff gene is altered, wherein a portion of the endogenous Baff gene is replaced with a heterologous sequence (e.g., a human BAFF gene sequence, in whole or in part). In some embodiments, all or substantially all of the endogenous Baff gene is replaced with a heterologous gene (e.g., a human BAFF gene). In some embodiments, a portion of a heterologous Baff gene is inserted into an endogenous non-human Baff gene. In some embodiments, the heterologous gene is a human gene.

A non-human animal of the present invention contains a human BAFF gene, in whole or in part, at an endogenous non-human Baff locus. Thus, such non-human animals can be described as having a humanized Baff gene. The replaced, inserted or modified endogenous Baff gene (i.e., the humanized Baff gene) can be detected using a variety of methods including, for example, PCR, Western blot, Southern blot, restriction fragment length polymorphism (RFLP), or a gain or loss of allele assay.

In various embodiments, a humanized Baff gene according to the present invention includes a Baff gene that has a third, fourth, fifth, and sixth exon each having a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to a third, fourth, fifth, and sixth exon that appear in a human BAFF gene of Table 3.

In various embodiments, a humanized Baff gene according to the present invention includes a Baff gene that has a nucleotide coding sequence (e.g., a cDNA sequence) at least 50% (e.g., 50%, 55%, 60%, 65%, 70%, 75%, 80%, 85%, 90%, 91%, 92%, 93%, 94%, 95%, 96%, 97%, 98%, 99% or more) identical to nucleotides 692-2671 that appear in a human BAFF cDNA sequence of Table 3.

In various embodiments, a humanized Baff protein produced by a non-human animal of the present invention has an extracellular portion having a sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to an extracellular portion of a human BAFF protein that appears in Table 3.

In various embodiments, a humanized Baff protein produced by a non-human animal of the present invention has an extracellular portion having a sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to amino acid residues 142 to 285 that appear in a human BAFF protein of Table 3.

In various embodiments, a humanized Baff protein produced by a non-human animal of the present invention has an amino acid sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to an amino acid sequence of a humanized. Baff protein that appears in Table 3.

In various embodiments, a humanized Baff protein produced by a non-human animal of the present invention has an amino acid sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to an amino acid sequence of a human BAFF protein that appears in Table 3.

Compositions and methods for making non-human animals that expresses a humanized Baff protein, including specific polymorphic forms or allelic variants (e.g., single amino acid differences, alternative splice variants, etc.), are provided, including compositions and methods for making non-human animals that expresses such proteins from a human promoter and a human regulatory sequence or, optionally, from a non-human promoter and a non-human regulatory sequence. In some embodiments, compositions and methods for making non-human animals that expresses such proteins from an endogenous promoter and an endogenous regulatory sequence are also provided. The methods include inserting the genetic material encoding a human BAFF protein, in whole or in part, at a precise location in the genome of a non-human animal that corresponds to an endogenous Baff gene thereby creating a humanized Baff gene that expresses a BAFF protein that is human, in whole or in part. In some embodiments, the methods include inserting genomic DNA corresponding to exons 3 to 6 of a human BAFF gene into an endogenous Baff gene of the non-human animal thereby creating a humanized gene that encodes a Baff protein that contains a human portion containing amino acids encoded by the inserted exons.

A humanized Baff gene approach employs a relatively minimal modification of the endogenous gene and results in natural Baff-mediated signal transduction in the non-human animal, in various embodiments, because the genomic sequence of the Baff gene is modified in a single fragment and therefore retain normal functionality by including necessary regulatory sequences. Thus, in such embodiments, the Baff gene modification does not affect other surrounding genes or other endogenous Baff genes. Further, in various embodiments, the modification does not affect the assembly of a functional transmembrane protein on the plasma membrane and maintains normal association with its receptors via binding and interaction of the extracellular portion with a given receptor which is unaffected by the modification.

A schematic illustration (not to scale) of endogenous murine and human BAFF genes is provided in FIG. 1. A schematic illustration (not to scale) of a humanized Baff gene is provided in FIG. 2. As illustrated, genomic DNA containing exons 3 to 6 of a human BAFF gene is inserted into an endogenous murine Baff gene by a targeting construct. This genomic DNA comprises the portion of the gene that encodes the extracellular portion (e.g., amino acid residues 142 to 285) of a human BAFF protein responsible for receptor binding.

Figure 2:
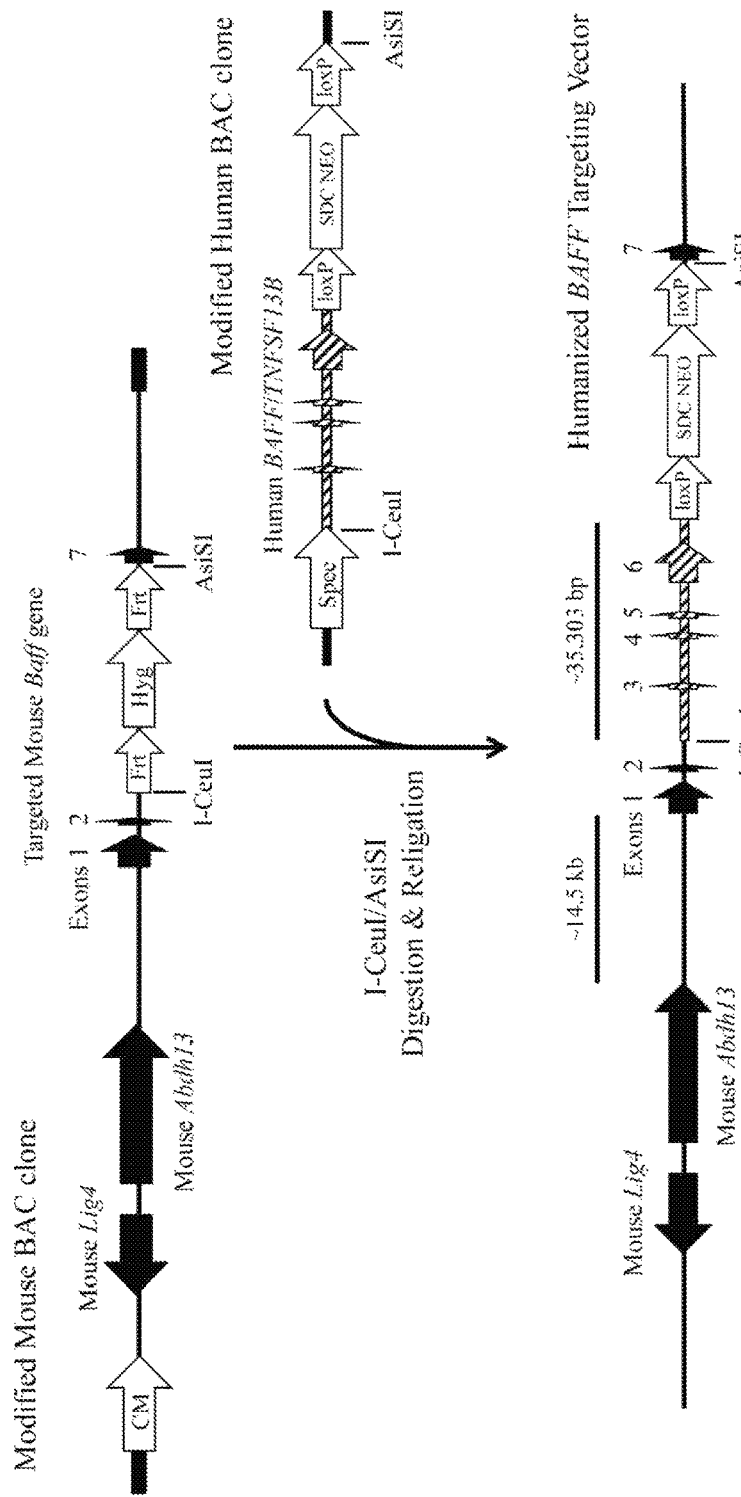
FIG. 2 shows a diagram, not to scale, of an exemplary method for humanization of a non-human B-cell Activating Factor (Baff) gene. Non-human sequences are shown as closed, black symbols. Human sequences are shown in open, diagonal filled symbols. CM: Chloramphenicol selection cassette. Hyg: hygromycin selection cassette. SDC NEO: self-deleting neomycin selection cassette. Spec: spectinomycin selection cassette. Frt: Flp recombinase target recognition site sequence. LoxP: Cre recombinase target recognition site sequence. Restriction enzyme recognition sites are indicated (e.g., AsiSI, I-CeuI, etc.).

A non-human animal (e.g., a mouse) having a humanized Baff gene can be made by any method known in the art. For example, a targeting vector can be made that introduces a human BAFF gene, in whole or in part, with a selectable marker gene. FIG. 2 illustrates a mouse genome comprising an insertion of exons 3 to 6 of a human BAFF gene. As illustrated, the targeting construct contains unique 5' and 3' restriction endonuclease sites which allow for the precise insertion of the human genetic material comprising exons 3 to 6 of a human BAFF gene. The targeting construct also contains a self-deleting drug selection cassette (e.g., a neomycin resistance gene flanked on both sides by LoxP sequences; see U.S. Pat. No. 8,354,389 and U.S. Pat. No. 8,518,392, both of which are herein incorporated by reference which is positioned 3' genetic material comprising exons 3 to 6 of a human BAFF gene. Upon digestion and religation, exons 3 to 6 of a human BAFF gene are inserted into an endogenous murine Baff gene that has been specifically engineered to accept the human sequence contained in the targeting vector. A humanized Baff gene is created resulting in a cell or non-human animal that expresses a humanized Baff protein that contains amino acids encoded by exons 3 to 6 of a human BAFF gene. The drug selection cassette will be removed in a development-dependent manner, i.e., progeny derived from mice whose germ line cells containing the humanized Baff gene described above will shed the selectable marker from differentiated cells during development.

The non-human animals of the present invention may be prepared as described above, or using methods known in the art, to comprise additional human or humanized genes, oftentimes depending on the intended use of the non-human animal. Genetic material of such additional human or humanized genes may be introduced through the further alteration of the genome of cells (e.g., embryonic stem cells) having the genetic modifications as described above or through breeding techniques known in the art with other genetically modified strains as desired. In some embodiments, non-human animals of the present invention are prepared to further comprise one or more human or humanized genes selected from BAFF-R, TACI, and BCMA. In some embodiments, non-human animals of the present invention are prepared to further comprise a human or humanized A PRoliferation-Inducing Ligand (APRIL) gene. In some embodiments, non-human animals of the present invention are prepared to further comprise a human or humanized TNF-related weak inducer of apoptosis (TWEAK). In some embodiments, non-human animals of the present invention comprise a humanized Baff gene as described herein and genetic material from a heterologous species (e.g., humans), wherein the genetic material encodes, in whole or in part, one or more heterologous proteins selected from BAFF-R, TACI, BCMA, APRIL and TWEAK.

In addition to mice having humanized Baff genes as described herein, also provided herein are other genetically modified non-human animals that comprise humanized Baff genes. In some embodiments, such non-human animals comprise a humanized Baff gene operably linked to an endogenous Baff promoter sequence. In some embodiments, such non-human animals express a humanized BAFF protein from an endogenous Baff locus, wherein the humanized Baff protein comprises amino acid residues 142 to 285 of a human BAFF protein.

Such non-human animals may be selected from the group consisting of a mouse, rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable ES cells are not readily available, other methods are employed to make a non-human animal comprising the genetic modifications as described herein. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo.

In some embodiments, a non-human animal of the present invention is a mammal. In some embodiments, a non-human animal of the present invention is a small mammal, e.g., of the superfamily Dipodoidea or Muroidea. In some embodiments, a genetically modified animal of the present invention is a rodent. In some embodiments, a rodent of the present invention is selected from a mouse, a rat, and a hamster. In some embodiments, a rodent of the present invention is selected from the superfamily Muroidea. In some embodiments, a genetically modified animal of the present invention is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rats, bamboo rats, and zokors). In some certain embodiments, a genetically modified rodent of the present invention is selected from a true mouse or rat (family Muridae), a gerbil, a spiny mouse, and a crested rat. In some certain embodiments, a genetically modified mouse of the present invention is from a member of the family Muridae. In some embodiment, an non-human animal of the present invention is a rodent. In some certain embodiments, a rodent of the present invention is selected from a mouse and a rat. In some embodiments, a non-human animal of the present invention is a mouse.

In some embodiments, a non-human animal of the present invention is a rodent that is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In some certain embodiments, a mouse of the present invention is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129/SvJae, 129S6 (129/SvEvTac), 129S7, 129S8, 129T1, 129T2 (see, e.g., Festing et al., 1999, Mammalian Genome 10:836; Auerbach et al., 2000, Biotechniques 29(5):1024-1028, 1030, 1032). In some certain embodiments, a genetically modified mouse of the present invention is a mix of an aforementioned 129 strain and an aforementioned C57BL/6 strain. In some certain embodiments, a mouse of the present invention is a mix of aforementioned 129 strains, or a mix of aforementioned BL/6 strains. In some certain embodiments, a 129 strain of the mix as described herein is a 129S6 (129/SvEvTac) strain. In some embodiments, a mouse of the present invention is a BALB strain, e.g., BALB/c strain. In some embodiments, a mouse of the present invention is a mix of a BALB strain and another aforementioned strain.

In some embodiments, a non-human animal of the present invention is a rat. In some certain embodiments, a rat of the present invention is selected from a Wistar rat, an LEA strain, a Sprague Dawley strain, a Fischer strain, F344, F6, and Dark Agouti. In some certain embodiments, a rat strain as described herein is a mix of two or more strains selected from the group consisting of Wistar, LEA, Sprague Dawley, Fischer, F344, F6, and Dark Agouti.

Methods Employing Non-Human Animals Having Humanized BAFF Genes

Baff transgenic non-human animals (e.g., mice) have been reported (Mackay et al., 1999, J. Exp. Med. 190(11):1697-1710; Khare et al., 2000, PNAS 97(7):3370-3375; Gavin et al., 2005, J. Immunol. 175:319-328). Such animals have been employed in a variety of assays to determine the molecular aspects of BAFF expression, function, and regulation. However, they are not without limitation. For example, use of Baff transgenic mice have been limited due to overexpression of murine Baff (e.g., full-length Baff or ΔBaff). Overexpression of Baff in transgenic mice leads to several B cell abnormalities characterized by, inter alia, excessive accumulation and activation of B cells, and auto-immune disease through proliferation of auto-reactive B cells. In some cases, transgenic mice overexpressing murine BAFF have increased levels of serum immunoglobulin (e.g., IgM, IgG, IgE, etc.). Further, transgenic mice overexpressing murine Baff demonstrate other abnormalities such as glomerulonephritis. Therefore, the molecular aspects of BAFF-mediated biological function and signaling pathways has not been exploited in transgenic mice.

Non-human animals of the present invention provide an improved in vivo system and source of biological materials (e.g., cells) expressing human BAFF that are useful for a variety of assays. In various embodiments, non-human animals of the present invention are used to develop therapeutics that target human BAFF and/or modulate BAFF-mediated signaling pathways. In various embodiments, mice of the present invention are used to screen and develop candidate therapeutics (e.g., antibodies) that bind to human BAFF. In various embodiments, non-human animals of the present invention are used to determine the binding profile of antagonists and/or agonists a humanized Baff on the surface of a cell of a non-human animal as described herein.

In various embodiments, non-human animals of the present invention are used to measure the therapeutic effect of blocking or modulating human BAFF signal transduction (e.g., phosphorylation) and the effect on gene expression as a result of cellular changes. In various embodiments, non-human animals of the present invention are used to measure the therapeutic effect of blocking or modulating human BAFF-BAFFR, BAFF-TACI, and/or BAFF-BCMA signaling pathways, for example, the modulation of NF-κB-mediated transcription of DNA. In various embodiments, a non-human animal of the present invention or cells isolated therefrom are exposed to a candidate therapeutic that binds to a human BAFF protein on the surface of a cell of the non-human animal and, after a subsequent period of time, analyzed for effects on BAFF-dependent processes, for example, B activation, regulation of the numbers of specific B cell subsets in various compartments (e.g., spleen, bone marrow, lymph node, etc.), survival of auto-reactive B cells, and NF-κB activation.

Non-human animals of the present invention express humanized Baff protein, thus cells, cell lines, and cell cultures can be generated to serve as a source of humanized Baff for use in binding and functional assays, e.g., to assay for binding or function of a BAFF antagonist or agonist, particularly where the antagonist or agonist is specific for a human BAFF sequence or epitope. In various embodiments, a humanized Baff protein expressed by a non-human animal as described herein may comprise a variant amino acid sequence. Variant human BAFF proteins having variations associated with ligand binding residues have been reported. In various embodiments, non-human animals of the present invention express a humanized Baff protein variant. In various embodiments, the variant is polymorphic at an amino acid position associated with ligand binding. In various embodiments, non-human animals of the present invention are used to determine the effect of ligand binding through interaction with a polymorphic variant of human BAFF. In some certain embodiments, non-human animals of the present invention express a human BAFF splice variant protein that appears in Table 3.

Cells from non-human animals of the present invention can be isolated and used on an ad hoc basis, or can be maintained in culture for many generations. For example, cells from non-human animals of the present invention can be used in a variety of cellular assays known in the art. In various embodiments, cells from a non-human animal of the present invention are immortalized and maintained in culture indefinitely (e.g., in serial cultures).

In various embodiments, cells and/or non-human animals of the present invention are used in a survival and/or proliferation assay (e.g., employing B or T cells) to screen and develop candidate therapeutics that modulate human BAFF. Survival of auto-reactive B cells plays an important role in the chronic pathology of autoimmune diseases, such as, for example, systemic lupus erythematosus (SLE), therefore, candidate BAFF modulators (e.g., antagonists) may be identified, characterized and developed using cells of non-human animals of the present invention and/or a non-human animal as described herein. In some embodiments, cells and/or non-human animals of the present invention are used in a survival assay to determine the number of antigen-specific plasma B cells in the presence and absence of BAFF.

In various embodiments, cells and/or non-human animals of the present invention are used in various immunization regimens to determine the BAFF-mediated functions in the immune response to an antigen. In some embodiments, candidate therapeutics that bind to, or block one or more functions of, human BAFF are characterized in a non-human animal of the present invention. Suitable measurements include various cellular assays, proliferation assays, serum immunoglobulin analysis (e.g., antibody titer), cytotoxicity assays, characterization of ligand-receptor interactions (immunoprecipitation assays). In some embodiments, non-human animals of the present invention are used to characterize the BAFF-mediated functions regulating an immune response to an antigen. In some embodiments, the antigen is associated with an autoimmune disease or condition. In some embodiments, the antigen is a test antigen (e.g., ovalbumin or OVA). In some embodiments, the antigen is a target associated with a disease or condition suffered by one or more human patients in need of treatment.

In various embodiments, non-human animals of the present invention are used in serum assays for determining titers of double-stranded DNA (dsDNA) autoantibody production for testing the pharmaco-toxicological aspects of candidate therapeutics that target human BAFF. In some embodiments, double-stranded DNA (dsDNA) autoantibody production in non-human animals of the present invention results from one or more autoimmune diseases or conditions induced in the non-human animal.

In various embodiments, cells and/or non-human animals of the present invention are used to characterize the repertoire and/or specificity of antibodies generated in an immune response to antigen. In some embodiments, the immune response is characterized by the generation of autoantibodies that are specific for one or more tissues of a non-human animal of the present invention. In some embodiments, the therapeutic potential of compounds or biological agents to modulate BAFF-dependent regulation of the B cell repertoire is characterized and/or developed in a non-human animal of the present invention.

In various embodiments, non-human animals of the present invention are used for challenge with one or more antigens to determine the therapeutic potential of compounds or biological agents to modulate BAH-dependent regulation of an immune response, including but not limited to, the specific T cell-dependent and B cell-dependent responses to a given antigen.

In various embodiments, non-human animals of the present invention are used in transplantation or adoptive transfer experiments to determine the therapeutic potential of compounds or biological agents to modulate BAH-dependent regulation of new lymphocytes and their immune function. In various embodiments, non-human animals of the present invention are transplanted with human B cells.

In various embodiments, cells of non-human animals of the present invention are used to in T cell assays to determine the therapeutic potential of compounds or biological agents to modulate BAFF-dependent regulation of T cell-dependent response and function. Exemplary T cell assays include, but are not limited to, ELISpot, intracellular cytokine staining, major histocompatibility complex (MHC) restriction, viral suppression assays, cytotoxicity assays, proliferation assays and regulatory T cell suppression assays.

In various embodiments, cells of non-human animals of the present invention are used in tumor cell growth assays to determine the therapeutic potential of compounds or biological agents to modulate BAFF-dependent regulation and/or stimulation of tumor cell growth.

In various embodiments, an autoimmune disease or condition is induced in one or non-human animals of the present invention to provide an in viva system for determining the therapeutic potential of compounds or biological agents to modulate BAFF-dependent regulation of one or more functions of the autoimmune disease or condition. In some embodiments, the autoimmune condition is an inflammatory condition, for example, arthritis (e.g., collagen-induced arthritis, CIA).

Non-human animals of the present invention provide an in vivo system for the analysis and testing of a drug or vaccine. In various embodiments, a candidate drug or vaccine may be delivered to one or more non-human animals of the present invention, followed by monitoring of the non-human animals to determine one or more of the immune response to the drug or vaccine, the safety profile of the drug or vaccine, or the effect on a disease or condition. Exemplary methods used to determine the safety profile include measurements of toxicity, optimal dose concentration, efficacy of the drug or vaccine, and possible risk factors. Such drugs or vaccines may be improved and/or developed in such non-human animals.

Non-human animals of the present invention provide an improved in viva system for the development and characterization of candidate therapeutics for use in cancer. In various embodiments, non-human animals of the present invention may be implanted with a tumor, followed by administration of a candidate therapeutic. The tumor may be allowed sufficient time to be established in one or more locations within the non-human animal. Tumor cell proliferation, growth, etc. may be measured both before and after administration with the candidate therapeutic. Cytotoxicity of candidate therapeutics may also be measured in the non-human animal as desired.

Non-human animals of the present invention provide an improved in vivo system for elucidating mechanisms of human cell-to-cell interaction through adoptive transfer. In various embodiments, non-human animals of the present invention may by implanted with a tumor xenograft, followed by a second implantation of tumor infiltrating lymphocytes in the non-human animals by adoptive transfer to determine the effectiveness in eradication of solid tumors or other malignancies. Such experiments may be done with human cells (e.g., B cell lymphomas) due to the exclusive presence of human BAFF without competition with endogenous Baff of the non-human animal. Further, therapies and pharmaceuticals for use in xenotransplantation can be improved and/or developed in such non-human animals.

Non-human animals of the present invention provide an improved in vivo system for maintenance and development of human hematopoietic stem cells through engraftment. In various embodiments, non-human animals of the present invention provide improved development and maintenance of human stem cells within the non-human animal. In various embodiments, increased populations of differentiated human B and T cells are observed in the blood, bone marrow, spleen and thymus of the non-human animal. In various embodiments, non-human animals of the present invention provide an increase in the level of engraftment of human hematopoietic stem cells as compared to non-human animals that express both endogenous non-human Baff and heterologous (e.g., human) BAFF.

Non-human animals of the present invention provide an improved in vivo system for maintenance and development of human B cells (e.g., from human donors) through engraftment. In various embodiments, non-human animals of the present invention provide improved development and maintenance of human B cells within the non-human animal. In various embodiments, increased populations of differentiated human B cells post-immunization are observed in one or more of the blood, bone marrow, spleen or a lymph node of the non-human animal. In various embodiments, non-human animals of the present invention provide an increase in the level of engraftment of human B cells as compared to non-human animals that express endogenous non-human Baff.

EXAMPLES

The following examples are provided so as to describe to those of ordinary skill in the art how to make and use methods and compositions of the invention, and are not intended to limit the scope of what the inventors regard as their invention. Unless indicated otherwise, temperature is indicated in Celsius, and pressure is at or near atmospheric.

Example 1. Humanization of an Endogenous Non-Human B-Cell Activating Factor (Baff) Gene This example illustrates exemplary methods of humanizing an endogenous gene encoding B-cell Activating Factor (Baff in a non-human animal such as a rodent (e.g., a mouse). Human BAFF is known to exist in several variant (or allelic) forms. The methods described in this example can be employed to humanize an endogenous Baff gene of a non-human animal using any human variant (or allele), or combination of human variants (or alleles or fragments thereof) as desired. In this example, a human BAFF gene that appears in bacterial artificial chromosome (BAC) clone CTD-2355n18 is employed for humanizing an endogenous Baff gene of a mouse.

A targeting vector for humanization of an extracellular region of a Baff gene was constructed using bacterial homologous recombination and VELOCIGENE® technology (see, e.g., U.S. Pat. No. 6,586,251 and Valenzuela et al., High-throughput engineering of the mouse genome coupled with high-resolution expression analysis, 2003, Nature Biotech. 21(6):652-659). An exemplary process for humanization of an endogenous Baff gene of a mouse is set forth in FIG. 2.

Briefly, a human bacterial artificial chromosome (BAC) clone CTD-2355n18 (Invitrogen) was modified to delete the 3' flanking region of the human BAFF gene starting at approximately 206 bp 3' of the human BAFF gene. The modification was performed by homologous recombination in bacterial cells using a targeting vector containing a self-deleting neomycin cassette flanked by recombinase recognition sites (e.g., LoxP; see U.S. Pat. No. 8,354,389 and U.S. Pat. No. 8,518,392, both of which are herein incorporated by reference) and a unique AsiSI restriction site positioned at the 3' of the cassette. The resulting modified BAC clone was modified in a second homologous recombination step in bacterial cells using a spectinomycin cassette to delete sequence 5' of the human BAFF gene and exons 1, 2 and approximately 3146 bp of intron 2. The spectinomycin cassette contained a unique I-CeuI site 3' of the spectinomycin cassette. Therefore, the double modified human BAC clone contained, from 5' to 3', a spectinomycin cassette, an I-CeuI site, approximately 35,303 bp of human genomic sequence containing most of human BAFF intron 2, human BAFF exons 3 to 6 and approximately 206 bp of human sequence 3' of human BAFF exon 6, and a self-deleting neomycin cassette flanked by LoxP sites, and a 3' AsiSI site.

Separately, a mouse BAC clone RP23-351L20 (Invitrogen) was modified to specifically insert the modified human BAC clone described above. In a first step, a hygromycin cassette flanked by site-specific recombinase recognition sites (e.g., Frt) was used to delete the sequence containing exons 3-6 and part of exon 7 of a mouse Baff gene. The 3'UTR and polyadenylation signal was retained. The hygromycin cassette included unique I-CeuI and AsiSI restriction sites at flanking 5' and 3' ends, respectively. Homologous recombination in bacterial cells with the hygromycin cassette resulted in a ~25,148 bp deletion in the mouse Baff gene corresponding to exons 3-7, leaving intact ~3069 bp of the mouse Baff intron 2. The 3' end of the hygromycin cassette was targeted to approximately the middle of the 3' UTR of the mouse Baff gene (of exon 7) in BAC clone RP23-351L20. The modified mouse BAC clone having a deletion of mouse Baff exons 3-6 and 7 (in part) from homologous recombination with the hygromycin cassette was modified in a second step using the modified human BAC clone having a deletion of human BAFF exons 1-2 and ~3146 bp of intron 2. This was achieved by through the unique restriction enzyme sites common between the two modified BAC clones. Each modified BAC clone was digested with I-CeuI and AsiSI to produce compatible cohesive fragments (FIG. 2). The final targeting vector, made by ligation of the compatible restriction fragments, contained, from 5' to 3', mouse genomic sequence containing mouse Lig4 and Abdh13 genes, ~14.5 kb of mouse genomic sequence, exons 1 and 2 of a mouse Baff gene, ~3069 bp of intron 2 of a mouse Baff gene, an I-CeuI site, ~35.3 kb of human genomic sequence containing exons 3 to 6 of a human BAFF gene, a self-deleting neomycin cassette flanked by recombinase recognition sites, an AsiSI site, part of a mouse Baff exon 7 that included a 3'UTR and polyadenylation signal, and mouse genomic sequence 3' of a mouse Baff gene.

The final targeting vector was used to electroporate BALB-Rag2$^{-/-}$IL2Rγc$^{-/-}$ (DKO) mouse embryonic stem (ES) cells to create modified ES cells comprising a Baff gene at an endogenous Baff locus that is humanized from approximately the middle of intron 2 of a mouse Baff gene (~3000 bp 3' of splice donor site) to approximately 100 bp 3' of the polyadenylation site of a human BAFF gene that was inserted into approximately the middle of the 3'UTR of a mouse Baff gene (FIG. 1). Positively targeted ES cells containing a humanized BAFF gene were identified by an assay (Valenzuela et al., supra) that detected the presence of the human BAFF sequence and confirmed loss of mouse Baff sequences. Table 4 sets forth the primers and probes that were used to confirm humanization of an endogenous Baff gene as described above. hBAFF: human BAFF; mBaff; mouse Baff.

Positive ES cell clones were then used to implant female mice using the VELOCIMOUSE® method (see, e.g., U.S. Pat. No. 7,294,754 and Poueymirou et al., F0 generation mice that are essentially fully derived from the donor gene-targeted ES cells allowing immediate phenotypic analyses, 2007, Nature Biotech. 25(1):91-99) to generate a litter of pups containing an insertion of exons 3 to 6 of a human BAFF gene into an endogenous Baff gene of a mouse. Mice bearing the humanization of exons 3 to 6 of an endogenous Baff gene were again confirmed identified by genotyping of DNA isolated from tail snips using a modification of allele assay (Valenzuela et al., supra) that detected the presence of the human BAFF gene sequences. Pups are genotyped and cohorts of animals heterozygous for the humanized Baff gene construct are selected for characterization.

TABLE 4

| Name | Location | Primer | Sequence (5'-3') | |
|---|---|---|---|---|
| mBaff-1 | mBaff intron 2 | Forward | GGACAGCAGATAGGAAAGCTTCTTG | SEQ ID NO: 8 |
| | | Reverse | GGGACGGACACTCATTTGAC | SEQ ID NO: 9 |
| | | Probe | TAGGAATCCCAGTCCTTAGAACCGCA | SEQ ID NO: 10 |

TABLE 4-continued

| Name | Location | Primer | Sequence (5'-3') | | |
|------|----------|--------|------------------|---|---|
| mBaff-2 | mBaff exon 7 | Forward | CCTCGGGAGAATGCACAGAT | SEQ ID NO: | 11 |
| | | Reverse | GCACTCCAGCAAGTGAGTTAC | SEQ ID NO: | 12 |
| | | Probe | TCACGCAACGGAGACGACACCTT | SEQ ID NO: | 13 |
| hBAFF-1 | hBAFF intron 2 | Forward | CCGGTTGGCATTTCTGGCTTAG | SEQ ID NO: | 14 |
| | | Reverse | GGCTGGATGGTCAAGTTCTACA | SEQ ID NO: | 15 |
| | | Probe | TTCCAGGCTGTAACATGAGTGTTGGA | SEQ ID NO: | 16 |
| hBAFF-2 | hBAFF intron 5 | Forward | ACACCAGACAGGTGACTTAGGAA | SEQ ID NO: | 17 |
| | | Reverse | GCTCCTGGGTGCAAAGGTA | SEQ ID NO: | 18 |
| | | Probe | TGCGAAAGTGTAGGCGCAAACC | SEQ ID NO: | 19 |

EQUIVALENTS

Having thus described several aspects of at least one embodiment of this invention, it is to be appreciated by those skilled in the art that various alterations, modifications, and improvements will readily occur to those skilled in the art. Such alterations, modifications, and improvements are intended to be part of this disclosure, and are intended to be within the spirit and scope of the invention. Accordingly, the foregoing description and drawing are by way of example only and the invention is described in detail by the claims that follow.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification.

Those skilled in the art will appreciate typical standards of deviation or error attributable to values obtained in assays or other processes described herein.

The publications, websites and other reference materials referenced herein to describe the background of the invention and to provide additional detail regarding its practice are hereby incorporated by reference.

What is claimed is:

1. A method of making a genetically modified mouse, comprising the steps of:
   (a) providing a mouse embryonic stem (ES) cell,
   (b) replacing a mouse genomic fragment comprising exons 3-6 of an endogenous mouse B-cell Activating Factor (Baff) gene at an endogenous mouse Baff locus in the mouse ES cell, with a human genomic fragment comprising exons 3-6 of a human BAFF gene to form a humanized Baff gene whose coding exons consist of exons 1-2 of said endogenous mouse Baff gene and exons 3-6 of said human BAFF gene, wherein the humanized Baff gene is under control of the mouse Baff promoter at said endogenous mouse Baff locus and encodes a humanized Baff protein comprising an extracellular portion of the human BAFF protein linked to an intracellular portion of the mouse Baff protein encoded by said endogenous mouse Baff gene, and wherein the extracellular portion of said human BAFF protein is at least 98% identical to the amino acid sequence as set forth in amino acids 142 to 285 of SEQ ID NO: 5;

(c) obtaining a modified mouse ES cell comprising said humanized Baff gene from step (b); and (d) generating a genetically modified mouse from the modified mouse ES cell obtained in step (c), wherein said genetically modified mouse expresses said humanized Baff protein.

2. The method of claim 1, wherein the extracellular portion of said human BAFF protein consists of amino acids 142 to 285 of SEQ ID NO: 5.

3. The method of claim 1, wherein said humanized Baff protein consists of the amino acid sequence as set forth in SEQ ID NO: 7.

4. The method of claim 1, wherein the genetically modified mouse does not detectably express a full-length endogenous mouse Baff protein.

5. A method of engrafting human hematopoietic stem cells into a mouse, comprising:

(a) providing a BALB $Rag2^{-/-}IL\text{-}2R\gamma^{-/-}$ mouse whose genome comprises a replacement of a mouse genomic fragment comprising exons 3-6 of an endogenous mouse Baff gene with a human genomic fragment comprising exons 3-6 of a human BAFF gene to form a humanized Baff gene, wherein the replacement is at an endogenous mouse Baff locus, wherein the humanized Baff gene is under control of the mouse Baff promoter at said endogenous mouse Baff locus and expresses in said mouse a humanized Baff protein comprising an extracellular portion of the human BAFF protein encoded by said human BAFF gene linked to an intracellular portion of the mouse Baff protein encoded by said mouse Baff gene, wherein the coding exons of the humanized Baff gene consist of exons 1-2 of said endogenous mouse Baff gene and exons 3-6 of said human BAFF gene, and wherein the extracellular portion of said human BAFF protein is at least 98% identical to the amino acid sequence as set forth in amino acids 142 to 285 of SEQ ID NO: 5; and (b) transplanting said human hematopoietic stem cells into the mouse.

6. The method of claim 5, further comprising a step of:

(c) assaying engraftment of said human hematopoietic stem cells in the mouse, wherein the step of assaying comprises comparing the engraftment of said human hematopoietic stem cells to the engraftment in one or more BALB $Rag2^{-/-}IL\text{-}2R\gamma^{-/-}$ mice whose genome does not comprise a humanized Baff gene that encodes an extracellular portion of a human BAFF protein linked to an intracellular portion of a mouse Baff protein.

7. The method of claim 5, wherein said human hematopoietic stem cells are transplanted intravenously, intraperitoneally, or subcutaneously.

8. The method of claim 5, wherein the extracellular portion of said human BAFF protein consists of amino acids 142 to 285 of SEQ ID NO: 5.

9. The method of claim 5, wherein said humanized Baff protein consists of the amino acid sequence as set forth in SEQ ID NO: 7.

10. The method of claim 5, wherein the genetically modified mouse does not detectably express a full-length endogenous mouse Baff protein.

* * * * *

SEQUENCE LISTING

```
<160> NUMBER OF SEQ ID NOS: 19

<210> SEQ ID NO 1
<211> LENGTH: 1710
<212> TYPE: DNA
<213> ORGANISM: Mus musculus

<400> SEQUENCE: 1
ggcacgaggc agattgagca atccatggaa ggccagagcc agagaaccta cttcagggta        60
gcaaaagatg cagaagaaag tcaggagagc gctcctgggg gaacccagcc ctgccatgct       120
ctgagggcag tctcccagga cacagatgac aggaaatgac ccaccctgt  ggtcacttac       180 tccaaaggcc tagaccttca aagtgctcct cgtggaatgg atgagtctgc aaagaccctg       240
ccaccaccgt gcctctgttt ttgctccgag aaaggagaag atatgaaagt gggatatgat       300
```

```
cccatcactc cgcagaagga ggagggtgcc tggtttggga tctgcaggga tggaaggctg    360
ctggctgcta ccctcctgct ggccctgttg tccagcagtt tcacagcgat gtccttgtac    420
cagttggctg ccttgcaagc agacctgatg aacctgcgca tggagctgca gagctaccga    480
ggttcagcaa caccagccgc cgcgggtgct ccagagttga ccgctggagt caaactcctg    540
acaccggcag ctcctcgacc ccacaactcc agccgcggcc acaggaacag acgcgctttc    600
cagggaccag aggaaacaga acaagatgta gacctctcag ctcctcctgc accatgcctg    660
cctggatgcc gccattctca acatgatgat aatggaatga acctcagaaa catcattcaa    720
gactgtctgc agctgattgc agacagcgac acgccgacta tacgaaaagg aacttacaca    780
tttgttccat ggcttctcag ctttaaaaga ggaaatgcct tggaggagaa agagaacaaa    840
atagtggtga ggcaaacagg ctatttcttc atctacagcc aggttctata cacggacccc    900
atctttgcta tgggtcatgt catccagagg aagaaagtac acgtctttgg ggacgagctg    960
agcctggtga ccctgttccg atgtattcag aatatgccca aaacactgcc caacaattcc    1020
tgctactcgg ctggcatcgc gaggctggaa gaaggagatg agattcagct tgcaattcct    1080
cgggagaatg cacagatttc acgcaacgga gacgacacct tctttggtgc cctaaaactg    1140
ctgtaactca cttgctggag tgcgtgatcc ccttccctcg tcttctctgt acctccgagg    1200
gagaaacaga cgactggaaa aactaaaaga tggggaaagc cgtcagcgaa agttttctcg    1260
tgacccgttg aatctgatcc aaaccaggaa atataacaga cagccacaac cgaagtgtgc    1320
catgtgagtt atgagaaacg gagcccgcgc tcagaaagac cggatgagga agaccgtttt    1380
ctccagtcct ttgccaacac gcaccgcaac cttgcttttt gccttgggtg acacatgttc    1440
agaatgcagg gagatttcct tgttttgcga tttgccatga aagagggcc acaactgca     1500 ggtcactgaa gcattcacgc taagtctcag gatttactct cccttctcat gctaagtaca    1560
cacacgctct tttccaggta atactatggg atactatgga aaggttgttt gttttttaaat   1620 ctagaagtct tgaactggca atagacaaaa atccttataa attcaagtgt aaaataaact    1680
taattaaaaa ggtttaagtg tgaaaaaaaa                                     1710
```

<210> SEQ ID NO 2
<211> LENGTH: 309
<212> TYPE: PRT
<213> ORGANISM: Mus musculus

<400> SEQUENCE: 2

```
Met Asp Glu Ser Ala Lys Thr Leu Pro Pro Cys Leu Cys Phe Cys
1               5                   10                  15

Ser Glu Lys Gly Glu Asp Met Lys Val Gly Tyr Asp Pro Ile Thr Pro
                20                  25                  30

Gln Lys Glu Glu Gly Ala Trp Phe Gly Ile Cys Arg Asp Gly Arg Leu
            35                  40                  45

Leu Ala Ala Thr Leu Leu Leu Ala Leu Leu Ser Ser Phe Thr Ala
        50                  55                  60

Met Ser Leu Tyr Gln Leu Ala Ala Leu Gln Ala Asp Leu Met Asn Leu
65                  70                  75                  80

Arg Met Glu Leu Gln Ser Tyr Arg Gly Ser Ala Thr Pro Ala Ala Ala
                85                  90                  95

Gly Ala Pro Glu Leu Thr Ala Gly Val Lys Leu Leu Thr Pro Ala Ala
            100                 105                 110

Pro Arg Pro His Asn Ser Ser Arg Gly His Arg Asn Arg Arg Ala Phe
```

```
            115                 120                 125
Gln Gly Pro Glu Glu Thr Glu Gln Asp Val Asp Leu Ser Ala Pro Pro
        130                 135                 140

Ala Pro Cys Leu Pro Gly Cys Arg His Ser Gln His Asp Asp Asn Gly
145                 150                 155                 160

Met Asn Leu Arg Asn Ile Ile Gln Asp Cys Leu Gln Leu Ile Ala Asp
                165                 170                 175

Ser Asp Thr Pro Thr Ile Arg Lys Gly Thr Tyr Thr Phe Val Pro Trp
            180                 185                 190

Leu Leu Ser Phe Lys Arg Gly Asn Ala Leu Glu Glu Lys Glu Asn Lys
        195                 200                 205

Ile Val Val Arg Gln Thr Gly Tyr Phe Phe Ile Tyr Ser Gln Val Leu
    210                 215                 220

Tyr Thr Asp Pro Ile Phe Ala Met Gly His Val Ile Gln Arg Lys Lys
225                 230                 235                 240

Val His Val Phe Gly Asp Glu Leu Ser Leu Val Thr Leu Phe Arg Cys
                245                 250                 255

Ile Gln Asn Met Pro Lys Thr Leu Pro Asn Asn Ser Cys Tyr Ser Ala
            260                 265                 270

Gly Ile Ala Arg Leu Glu Glu Gly Asp Glu Ile Gln Leu Ala Ile Pro
        275                 280                 285

Arg Glu Asn Ala Gln Ile Ser Arg Asn Gly Asp Asp Thr Phe Phe Gly
    290                 295                 300

Ala Leu Lys Leu Leu
305

<210> SEQ ID NO 3
<211> LENGTH: 290
<212> TYPE: PRT
<213> ORGANISM: Mus musculus

<400> SEQUENCE: 3

Met Asp Glu Ser Ala Lys Thr Leu Pro Pro Pro Cys Leu Cys Phe Cys
1               5                   10                  15

Ser Glu Lys Gly Glu Asp Met Lys Val Gly Tyr Asp Pro Ile Thr Pro
            20                  25                  30

Gln Lys Glu Glu Gly Ala Trp Phe Gly Ile Cys Arg Asp Gly Arg Leu
        35                  40                  45

Leu Ala Ala Thr Leu Leu Leu Ala Leu Leu Ser Ser Phe Thr Ala
    50                  55                  60

Met Ser Leu Tyr Gln Leu Ala Ala Leu Gln Ala Asp Leu Met Asn Leu
65                  70                  75                  80

Arg Met Glu Leu Gln Ser Tyr Arg Gly Ser Ala Thr Pro Ala Ala Ala
                85                  90                  95

Gly Ala Pro Glu Leu Thr Ala Gly Val Lys Leu Leu Thr Pro Ala Ala
            100                 105                 110

Pro Arg Pro His Asn Ser Ser Arg Gly His Arg Asn Arg Arg Ala Phe
        115                 120                 125

Gln Gly Pro Glu Glu Thr Glu Gln Asp Val Asp Leu Ser Ala Pro Pro
    130                 135                 140

Ala Pro Cys Leu Pro Gly Cys Arg His Ser Gln His Asp Asp Asn Gly
145                 150                 155                 160

Met Asn Leu Arg Asn Arg Thr Tyr Thr Phe Val Pro Trp Leu Leu Ser
                165                 170                 175
```

```
Phe Lys Arg Gly Asn Ala Leu Glu Glu Lys Glu Asn Lys Ile Val Val
            180                 185                 190

Arg Gln Thr Gly Tyr Phe Phe Ile Tyr Ser Gln Val Leu Tyr Thr Asp
        195                 200                 205

Pro Ile Phe Ala Met Gly His Val Ile Gln Arg Lys Lys Val His Val
    210                 215                 220

Phe Gly Asp Glu Leu Ser Leu Val Thr Leu Phe Arg Cys Ile Gln Asn
225                 230                 235                 240

Met Pro Lys Thr Leu Pro Asn Asn Ser Cys Tyr Ser Ala Gly Ile Ala
                245                 250                 255

Arg Leu Glu Glu Gly Asp Glu Ile Gln Leu Ala Ile Pro Arg Glu Asn
            260                 265                 270

Ala Gln Ile Ser Arg Asn Gly Asp Asp Thr Phe Phe Gly Ala Leu Lys
        275                 280                 285

Leu Leu
    290

<210> SEQ ID NO 4
<211> LENGTH: 2675
<212> TYPE: DNA
<213> ORGANISM: Homo sapiens

<400> SEQUENCE: 4
```

| | | | | | |
|---|---|---|---|---|---|
| gaaattctta | caaaaactga | aagtgaaatg | aggaagacag | attgagcaat | ccaatcggag | 60 |
| ggtaaatgcc | agcaaaccta | ctgtacagta | ggggtagaga | tgcagaaagg | cagaaggag | 120 |
| aaaattcagg | ataactctcc | tgaggggtga | gccaagccct | gccatgtagt | gcacgcagga | 180 |
| catcaacaaa | cacagataac | aggaaatgat | ccattccctg | tggtcactta | ttctaaaggc | 240 |
| cccaaccttc | aaagttcaag | tagtgatatg | gatgactcca | cagaaaggga | gcagtcacgc | 300 |
| cttacttctt | gccttaagaa | aagagaagaa | atgaaactga | aggagtgtgt | ttccatcctc | 360 |
| ccacggaagg | aaagcccctc | tgtccgatcc | tccaaagacg | gaaagctgct | ggctgcaacc | 420 |
| ttgctgctgg | cactgctgtc | ttgctgcctc | acggtggtgt | ctttctacca | ggtggccgcc | 480 |
| ctgcaagggg | acctggccag | cctccgggca | gagctgcagg | gccaccacgc | ggagaagctg | 540 |
| ccagcaggag | caggagcccc | caaggccggc | ctggaggaag | ctccagctgt | caccgcggga | 600 |
| ctgaaaatct | tgaaccacc | agctccagga | gaaggcaact | ccagtcagaa | cagcagaaat | 660 |
| aagcgtgccg | ttcagggtcc | agaagaaaca | gtcactcaag | actgcttgca | actgattgca | 720 |
| gacagtgaaa | caccaactat | acaaaaagga | tcttacacat | tgttccatg | gcttctcagc | 780 |
| tttaaaggg | gaagtgccct | agaagaaaaa | gagaataaaa | tattggtcaa | agaaactggt | 840 |
| tactttttta | tatatggtca | ggttttatat | actgataaga | cctacgccat | gggacatcta | 900 |
| attcagagga | agaaggtcca | tgtctttggg | gatgaattga | gtctggtgac | tttgtttcga | 960 |
| tgtattcaaa | atatgcctga | aacactaccc | aataattcct | gctattcagc | tggcattgca | 1020 |
| aaactggaag | aaggagatga | actccaactt | gcaataccaa | gagaaaatgc | acaaatatca | 1080 |
| ctggatggag | atgtcacatt | ttttggtgca | ttgaaactgc | tgtgacctac | ttacaccatg | 1140 |
| tctgtagcta | ttttcctccc | tttctctgta | cctctaagaa | gaaagaatct | aactgaaaat | 1200 |
| accaaaaaaa | aaaaaaaaaa | aaaaaaaaaa | aaaagtagtt | accattgcct | ttctgtgag | 1260 |
| ctatttgttt | tggtttgctg | aaactagtcc | aaaacaggaa | atttaacaga | cagccacagc | 1320 |
| caaagagtgt | catgtgaatt | acaagaaata | gagcccattt | agggaaagat | agaactagaa | 1380 |
| aggcttttca | ttataattcc | atgttgaaca | attgagtcat | agcttcttat | cttggaggaa | 1440 |

-continued

```
ggacacaatt caaaggggca gtaaggattt tgtaaaacgt ggcatccata atttactatg      1500
gagcaagtgc ccacatctct aggacattaa gacatttatg agaaatctca ggattcatct      1560
tctgttttta tgttaaatgc actccctcct tttcagttaa cattataaaa agtaaaaaat      1620
gaaaatttta gaaatcttgc attagacaca tgaaaaaata actaaaagtt taaatttaaa      1680
tatgaaacaa ttttgctgaa aatagtatcc atatactatt taagtctttt atggttattt      1740
caagtataca atttctatct gtaatgtaat atattaccca cattttttt tcacaggaga       1800 gagagaatat cctcatttgt ttatgctcat gtgtattttc tatagtgaat ttcagaaact      1860
tttaatatca ggtaatttca atttatgcct ataaagcatt gattgaaaaa taactagaat      1920
tgtgcatata taacacataa tctccaacag aagttactga atacattcat actaatgtaa     1980
tgtaatttcc ctttatttct tgctcttctg tttcaaactg ctgctattgt agtttacata     2040
tcccaacctt taaaaatatt cctcttatta gctttatatt cactttatag aagttgagtt    2100
ttaattaaaa ttcttggcat cctgaagtat gtcacatagc atgtgctcct tataaatatg    2160
ttgatatctc agaagacagc atcccggttt tcattttata aagtaccata cttaagaatg    2220
ctgtaatact tatcttttat aacatgtttc cttcgctttg cttgtctttt atgtcatcag    2280
ttttaactgt ttacttcatt taacagttta catcattcaa cagtttactt cattaaacag   2340
taggtggaaa aatagatgcc agtctatgaa aatcttccca tctatatcaa aatactttc    2400 aaggatatac ttttcaaaac aaacgattta aattttatgt ttaaaatata aactttagat   2460
ttaaacttta tttaaatatc tggttcctat gattttgact tcagtaagtt caaataaaat   2520
atattttgca attcattttt acattataat ttaaaaagaa gaagcgataa gtggagtcag   2580
tttcaatgct aggtggggtg gttaatgatt tttctggtgt tgctgctaat gtggattaac   2640
aaataaaaac attcattgcc ttttgcctca taaaa                              2675
```

<210> SEQ ID NO 5
<211> LENGTH: 285
<212> TYPE: PRT
<213> ORGANISM: Homo sapiens

<400> SEQUENCE: 5

```
Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys Leu Leu
        35                  40                  45

Ala Ala Thr Leu Leu Leu Ala Leu Leu Ser Cys Cys Leu Thr Val Val
    50                  55                  60

Ser Phe Tyr Gln Val Ala Ala Leu Gln Gly Asp Leu Ala Ser Leu Arg
65                  70                  75                  80

Ala Glu Leu Gln Gly His His Ala Glu Lys Leu Pro Ala Gly Ala Gly
                85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
        115                 120                 125

Ser Arg Asn Lys Arg Ala Val Gln Gly Pro Glu Glu Thr Val Thr Gln
    130                 135                 140

Asp Cys Leu Gln Leu Ile Ala Asp Ser Glu Thr Pro Thr Ile Gln Lys
```

```
            145                 150                 155                 160
    Gly Ser Tyr Thr Phe Val Pro Trp Leu Leu Ser Phe Lys Arg Gly Ser
                    165                 170                 175

Ala Leu Glu Glu Lys Glu Asn Lys Ile Leu Val Lys Glu Thr Gly Tyr
                    180                 185                 190

Phe Phe Ile Tyr Gly Gln Val Leu Tyr Thr Asp Lys Thr Tyr Ala Met
                    195                 200                 205

Gly His Leu Ile Gln Arg Lys Val His Val Phe Gly Asp Glu Leu
                    210                 215                 220

Ser Leu Val Thr Leu Phe Arg Cys Ile Gln Asn Met Pro Glu Thr Leu
    225                 230                 235                 240

Pro Asn Asn Ser Cys Tyr Ser Ala Gly Ile Ala Lys Leu Glu Glu Gly
                    245                 250                 255

Asp Glu Leu Gln Leu Ala Ile Pro Arg Glu Asn Ala Gln Ile Ser Leu
                    260                 265                 270

Asp Gly Asp Val Thr Phe Phe Gly Ala Leu Lys Leu Leu
                    275                 280                 285

<210> SEQ ID NO 6
<211> LENGTH: 266
<212> TYPE: PRT
<213> ORGANISM: Homo sapiens

<400> SEQUENCE: 6

Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
                20                  25                  30

Arg Lys Glu Ser Pro Ser Val Arg Ser Ser Lys Asp Gly Lys Leu Leu
                35                  40                  45

Ala Ala Thr Leu Leu Leu Ala Leu Leu Ser Cys Cys Leu Thr Val Val
                50                  55                  60

Ser Phe Tyr Gln Val Ala Ala Leu Gln Gly Asp Leu Ala Ser Leu Arg
65                  70                  75                  80

Ala Glu Leu Gln Gly His His Ala Glu Lys Leu Pro Ala Gly Ala Gly
                85                  90                  95

Ala Pro Lys Ala Gly Leu Glu Glu Ala Pro Ala Val Thr Ala Gly Leu
                100                 105                 110

Lys Ile Phe Glu Pro Pro Ala Pro Gly Glu Gly Asn Ser Ser Gln Asn
                115                 120                 125

Ser Arg Asn Lys Arg Ala Val Gln Gly Pro Glu Glu Thr Gly Ser Tyr
                130                 135                 140

Thr Phe Val Pro Trp Leu Leu Ser Phe Lys Arg Gly Ser Ala Leu Glu
145                 150                 155                 160

Glu Lys Glu Asn Lys Ile Leu Val Lys Glu Thr Gly Tyr Phe Phe Ile
                165                 170                 175

Tyr Gly Gln Val Leu Tyr Thr Asp Lys Thr Tyr Ala Met Gly His Leu
                180                 185                 190

Ile Gln Arg Lys Lys Val His Val Phe Gly Asp Glu Leu Ser Leu Val
                195                 200                 205

Thr Leu Phe Arg Cys Ile Gln Asn Met Pro Glu Thr Leu Pro Asn Asn
                210                 215                 220

Ser Cys Tyr Ser Ala Gly Ile Ala Lys Leu Glu Glu Gly Asp Glu Leu
225                 230                 235                 240
```

Gln Leu Ala Ile Pro Arg Glu Asn Ala Gln Ile Ser Leu Asp Gly Asp
            245                 250                 255

Val Thr Phe Phe Gly Ala Leu Lys Leu Leu
            260                 265

<210> SEQ ID NO 7
<211> LENGTH: 278
<212> TYPE: PRT
<213> ORGANISM: Artificial Sequence
<220> FEATURE:
<223> OTHER INFORMATION: Humanized BAFF Protein

<400> SEQUENCE: 7

Met Asp Glu Ser Ala Lys Thr Leu Pro Pro Cys Leu Cys Phe Cys
1               5                   10                  15

Ser Glu Lys Gly Glu Asp Met Lys Val Gly Tyr Asp Pro Ile Thr Pro
            20                  25                  30

Gln Lys Glu Glu Gly Ala Trp Phe Gly Ile Cys Arg Asp Gly Arg Leu
        35                  40                  45

Leu Ala Ala Thr Leu Leu Ala Leu Leu Ser Ser Phe Thr Ala
    50                  55                  60

Met Ser Leu Tyr Gln Leu Ala Ala Leu Gln Ala Asp Leu Met Asn Leu
65                  70                  75                  80

Arg Met Glu Leu Gln Ser Tyr Arg Gly Ser Ala Thr Pro Ala Ala Ala
                85                  90                  95

Gly Ala Pro Glu Leu Thr Ala Gly Val Lys Leu Leu Thr Pro Ala Ala
            100                 105                 110

Pro Arg Pro His Asn Ser Ser Arg Gly His Arg Asn Arg Arg Ala Phe
        115                 120                 125

Gln Gly Pro Glu Glu Thr Val Thr Gln Asp Cys Leu Gln Leu Ile Ala
    130                 135                 140

Asp Ser Glu Thr Pro Thr Ile Gln Lys Gly Ser Tyr Thr Phe Val Pro
145                 150                 155                 160

Trp Leu Leu Ser Phe Lys Arg Gly Ser Ala Leu Glu Glu Lys Glu Asn
                165                 170                 175

Lys Ile Leu Val Lys Glu Thr Gly Tyr Phe Phe Ile Tyr Gly Gln Val
            180                 185                 190

Leu Tyr Thr Asp Lys Thr Tyr Ala Met Gly His Leu Ile Gln Arg Lys
        195                 200                 205

Lys Val His Val Phe Gly Asp Glu Leu Ser Leu Val Thr Leu Phe Arg
    210                 215                 220

Cys Ile Gln Asn Met Pro Glu Thr Leu Pro Asn Asn Ser Cys Tyr Ser
225                 230                 235                 240

Ala Gly Ile Ala Lys Leu Glu Glu Gly Asp Glu Leu Gln Leu Ala Ile
                245                 250                 255

Pro Arg Glu Asn Ala Gln Ile Ser Leu Asp Gly Asp Val Thr Phe Phe
            260                 265                 270

Gly Ala Leu Lys Leu Leu
        275

<210> SEQ ID NO 8
<211> LENGTH: 25
<212> TYPE: DNA
<213> ORGANISM: Artificial Sequence
<220> FEATURE:
<223> OTHER INFORMATION: Synthetic Oligonucleotide: mBaff-1, mBaff
      intron 2, Forward

<400> SEQUENCE: 8
ggacagcaga taggaaagct tcttg　　　　　　　　　　　　　　　　　　　　　25

<210> SEQ ID NO 9
<211> LENGTH: 20
<212> TYPE: DNA
<213> ORGANISM: Artificial Sequence
<220> FEATURE:
<223> OTHER INFORMATION: Synthetic Oligonucleotide: mBaff-1, mBaff
      intron 2, Reverse

<400> SEQUENCE: 9
gggacggaca ctcatttgac　　　　　　　　　　　　　　　　　　　　　　　　20

<210> SEQ ID NO 10
<211> LENGTH: 26
<212> TYPE: DNA
<213> ORGANISM: Artificial Sequence
<220> FEATURE:
<223> OTHER INFORMATION: Synthetic Oligonucleotide: mBaff-1, mBaff
      intron 2, Probe

<400> SEQUENCE: 10
taggaatccc agtccttaga accgca　　　　　　　　　　　　　　　　　　　　　26

<210> SEQ ID NO 11
<211> LENGTH: 20
<212> TYPE: DNA
<213> ORGANISM: Artificial Sequence
<220> FEATURE:
<223> OTHER INFORMATION: Synthetic Oligonucleotide: mBaff-2, mBaff
      exon 7, Forward

<400> SEQUENCE: 11
cctcgggaga atgcacagat　　　　　　　　　　　　　　　　　　　　　　　　20

<210> SEQ ID NO 12
<211> LENGTH: 21
<212> TYPE: DNA
<213> ORGANISM: Artificial Sequence
<220> FEATURE:
<223> OTHER INFORMATION: Synthetic Oligonucleotide: mBaff-2, mBaff
      exon 7, Reverse

<400> SEQUENCE: 12
gcactccagc aagtgagtta c　　　　　　　　　　　　　　　　　　　　　　　　21

<210> SEQ ID NO 13
<211> LENGTH: 23
<212> TYPE: DNA
<213> ORGANISM: Artificial Sequence
<220> FEATURE:
<223> OTHER INFORMATION: Synthetic Oligonucleotide: mBaff-2, mBaff
      exon 7, Probe

<400> SEQUENCE: 13
tcacgcaacg gagacgacac ctt　　　　　　　　　　　　　　　　　　　　　　　23

<210> SEQ ID NO 14
<211> LENGTH: 22
<212> TYPE: DNA
<213> ORGANISM: Artificial Sequence
<220> FEATURE:
<223> OTHER INFORMATION: Synthetic Oligonucleotide: hBaff-1, hBAFF
      intron 2, Forward

<400> SEQUENCE: 14

```
ccggttggca tttctggctt ag                                              22

<210> SEQ ID NO 15
<211> LENGTH: 22
<212> TYPE: DNA
<213> ORGANISM: Artificial Sequence
<220> FEATURE:
<223> OTHER INFORMATION: Synthetic Oligonucleotide: hBaff-1, hBAFF
      intron 2, Reverse

<400> SEQUENCE: 15
ggctggatgg tcaagttcta ca                                              22

<210> SEQ ID NO 16
<211> LENGTH: 26
<212> TYPE: DNA
<213> ORGANISM: Artificial Sequence
<220> FEATURE:
<223> OTHER INFORMATION: Synthetic Oligonucleotide: hBaff-1, hBAFF
      intron 2, Probe

<400> SEQUENCE: 16
ttccaggctg taacatgagt gttgga                                          26

<210> SEQ ID NO 17
<211> LENGTH: 23
<212> TYPE: DNA
<213> ORGANISM: Artificial Sequence
<220> FEATURE:
<223> OTHER INFORMATION: Synthetic Oligonucleotide: hBaff-2, hBAFF
      intron 5, Forward

<400> SEQUENCE: 17
acaccagaca ggtgacttag gaa                                             23

<210> SEQ ID NO 18
<211> LENGTH: 19
<212> TYPE: DNA
<213> ORGANISM: Artificial Sequence
<220> FEATURE:
<223> OTHER INFORMATION: Synthetic Oligonucleotide: hBaff-2, hBAFF
      intron 5, Reverse

<400> SEQUENCE: 18
gctcctgggt gcaaaggta                                                  19

<210> SEQ ID NO 19
<211> LENGTH: 22
<212> TYPE: DNA
<213> ORGANISM: Artificial Sequence
<220> FEATURE:
<223> OTHER INFORMATION: Synthetic Oligonucleotide: hBaff-2, hBAFF
      intron 5, Probe

<400> SEQUENCE: 19
tgcgaaagtg taggcgcaaa cc                                              22
```